United States Patent [19]

Leone-Bay et al.

[11] Patent Number: 6,051,561
[45] Date of Patent: Apr. 18, 2000

[54] COMPOUNDS AND COMPOSITIONS FOR DELIVERING ACTIVE AGENTS

[75] Inventors: Andrea Leone-Bay, Ridgefield, Conn.; Eric Wang, Yonkers, N.Y.; Donald J. Sarubbi, Bronxville, N.Y.; Harry Leipold, Elmsford, N.Y.

[73] Assignee: Emisphere Technologies Inc., Hawthorne, N.Y.

[21] Appl. No.: 08/797,813

[22] Filed: Feb. 7, 1997

[51] Int. Cl.[7] .................. A61K 31/725; A61K 38/00; A61K 39/00; A01N 43/04

[52] U.S. Cl. .................. 514/56; 514/54; 514/62; 530/300; 530/303; 530/351; 530/387.2; 530/399; 424/184.1

[58] Field of Search .................. 514/54, 56, 62; 530/300, 303, 351, 387.2, 399; 424/184.1

[56] References Cited

U.S. PATENT DOCUMENTS

| | | | |
|---|---|---|---|
| 3,687,926 | 8/1972 | Arima et al. | 530/329 |
| 4,908,233 | 3/1990 | Takizawa et al. | 427/213.35 |
| 5,536,813 | 7/1996 | Charpenel et al. | 530/324 |
| 5,705,529 | 1/1998 | Matyus et al. | |

FOREIGN PATENT DOCUMENTS

| | | |
|---|---|---|
| 2343037 | 3/1975 | Germany. |
| 6-107682 | 4/1994 | Japan. |
| WO 96/30036 | 10/1996 | WIPO. |

OTHER PUBLICATIONS

Kondo, *Microcapsule Processing and Technology*, pp. 154–165, 1979.
Pastores et al., *Journal of Liquid Chromatography*, 18:3049–3059, 1995.
Sinha et al., *Journal of Biological Chemistry*, 260:10714–10719, 1985.
Chemical Abstracts, vol. 99, No. 23, issued Dec. 5, 1983, Linfield et al, Antibacterially active substituted anilides of carboxylic and sulfonic acid, p. 455, columns 1 and 2, abstract No. 191473h, J. Med. Chem, 1983, 26(12), 1741–6 (Eng), 1983.
Franssen et al., J. Med. Chem., 35:1246–1259, 1992.

*Primary Examiner*—John Kight
*Assistant Examiner*—Everett White
*Attorney, Agent, or Firm*—Darby & Darby

[57] ABSTRACT

Carrier compounds and compositions therewith which are useful in the delivery of active agents are provided. Methods of administration and preparation are provided as well.

25 Claims, No Drawings

COMPOUNDS AND COMPOSITIONS FOR DELIVERING ACTIVE AGENTS

FIELD OF THE INVENTION

The present invention relates to compounds for delivering active agents, and particularly biologically or chemically active agents. These compounds are used as carriers to facilitate the delivery of a cargo to a target. The carrier compounds are well suited to form non-covalent mixtures with biologically-active agents for oral administration to animals. Methods for the preparation administration of such compositions are also disclosed.

BACKGROUND OF THE INVENTION

Conventional means for delivering active agents are often severely limited by biological, chemical, and physical barriers. Typically, these barriers are imposed by the environment through which delivery occurs, the environment of the target for delivery, or the target itself. Biologically or chemically active agents are particularly vulnerable to such barriers.

For example in the delivery to animals of biologically active or chemically active pharmacological and therapeutic agents, barriers are imposed by the body. Examples of physical barriers are the skin and various organ membranes that must be traversed before reaching a target. Chemical barriers include, but are not limited to, pH variations, lipid bi-layers, and degrading enzymes.

These barriers are of particular significance in the design of oral delivery systems. Oral delivery of many biologically or chemically active agents would be the route of choice for administration to animals if not for biological, chemical, and physical barriers such as varying pH in the gastro-intestinal (GI) tract, powerful digestive enzymes, and active agent impermeable gastrointestinal membranes. Among the numerous agents which are not typically amenable to oral administration are biologically or chemically active peptides, such as calcitonin and insulin; polysaccharides, and in particular mucopolysaccharides including, but not limited to, heparin; heparinoids; antibiotics; and other organic substances. These agents are rapidly rendered ineffective or are destroyed in the gastro-intestinal tract by acid hydrolysis, enzymes, or the like.

Earlier methods for orally administering vulnerable pharmacological agents have relied on the co-administration of adjuvants (e.g., resorcinols and non-ionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation.

Liposomes have also been described as drug delivery systems for insulin and heparin. See, for example, U.S. Pat. No. 4,239,754; Patel et al. (1976), *FEBS Letters,* Vol. 62, pg. 60; and Hashimoto et al. (1979), *Endocrinology Japan,* Vol. 26, pg. 337.

However, broad spectrum use of such drug delivery systems is precluded because: (1) the systems require toxic amounts of adjuvants or inhibitors; (2) suitable low molecular weight cargos, i.e. active agents, are not available; (3) the systems exhibit poor stability and inadequate shelf life; (4) the systems are difficult to manufacture; (5) the systems fail to protect the active agent (cargo); (6) the systems adversely alter the active agent; or (7) the systems fail to allow or promote absorption of the active agent.

More recently, microspheres of artificial polymers of mixed amino acids (proteinoids) have been used to deliver pharmaceuticals. For example, U.S. Pat. No. 4,925,673 describes drug-containing proteinoid microsphere carriers as well as methods for their preparation and use. These proteinoid microspheres are useful for the delivery of a number of active agents.

There is still a need in the art for simple, inexpensive delivery systems which are easily prepared and which can deliver a broad range of active agents.

SUMMARY OF THE INVENTION

Compounds and compositions which are useful in the delivery of active agents are provided. These compositions include at least one active agent, preferably a biologically or chemically active agent, and at least one of the following compounds 1–193, or salts thereof.

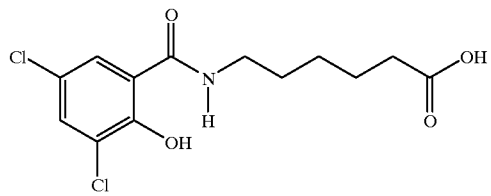

6-N-(3,5-dichloro-2-hydroxybenzoyl)aminocaproic acid

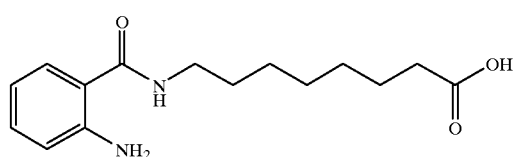

8(2-aminobenzoylamino)caprylic acid

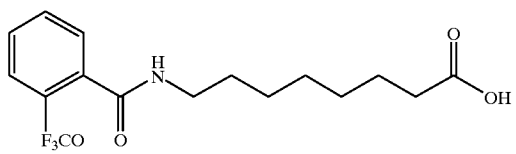
8(2-trifluoromethoxy)benzoylamino caprylic acid
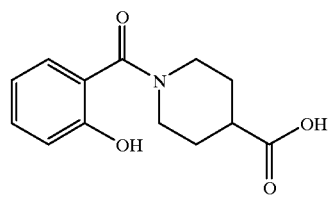
N-(2-hydroxybenzoyl)isonipecotic acid
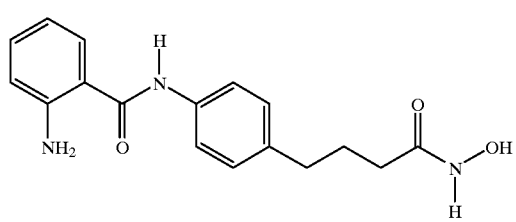
4-[4-(2-aminobenzoylamino)phenyl]butyrylhydroxamic acid
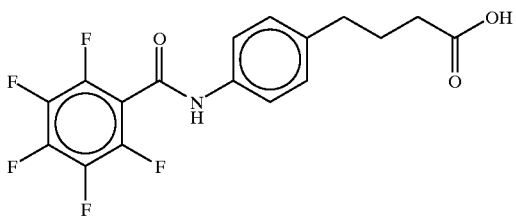
4-(4-(pentafluorobenzoyl)aminophenyl)butyric acid
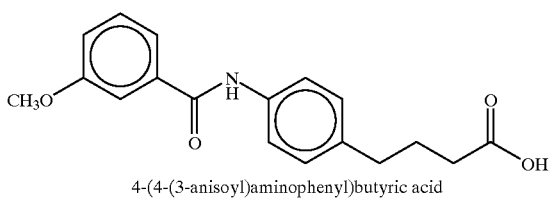
4-(4-(3-anisoyl)aminophenyl)butyric acid
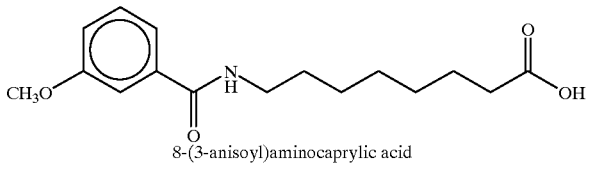
8-(3-anisoyl)aminocaprylic acid
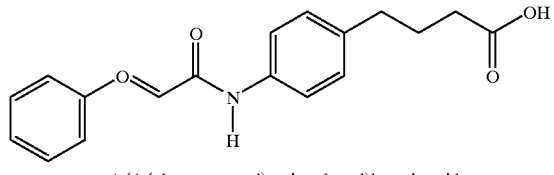
4-(4-(phenoxyacetyl)aminophenyl)butyric acid -continued
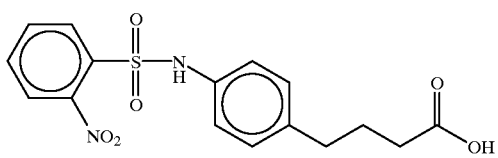
4-(4-(2-nitrobenzenesulfonyl)aminophenyl)butyric acid
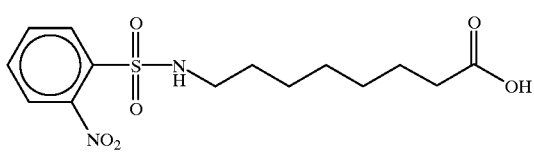
8-(2-nitrobenzenesulfonyl)aminocaprylic acid
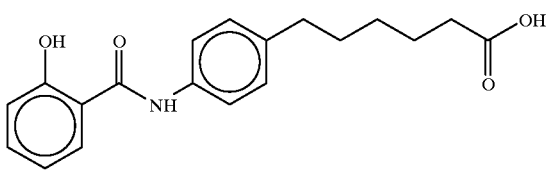
6-(4-(salicyloyl)aminophenyl)hexanoic acid
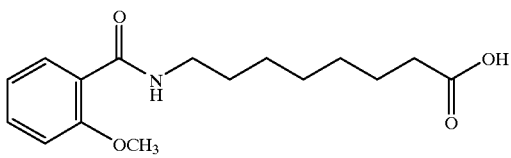
8-(2-methoxylbenzoyl)amino caprylic acid
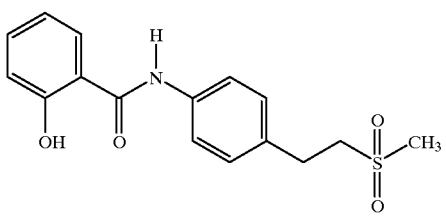
2-[4-Salicyloylamino)phenyl]ethyl methyl sulfone
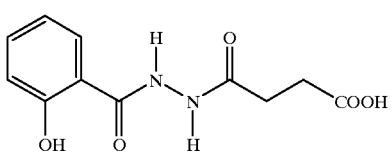
1-Salicyloyl-2-succinyl hydrazide
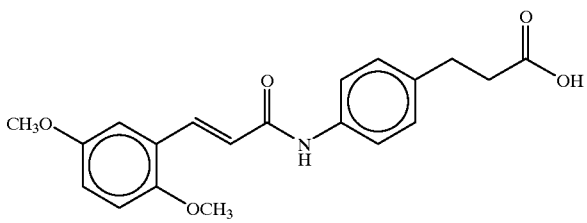
3-(4-(2,5-dimethoxycinnamoyl)aminophenyl)propionic acid

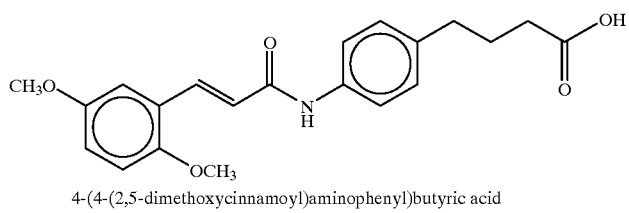
4-(4-(2,5-dimethoxycinnamoyl)aminophenyl)butyric acid
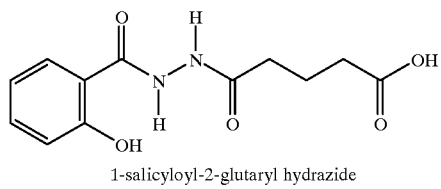
1-salicyloyl-2-glutaryl hydrazide
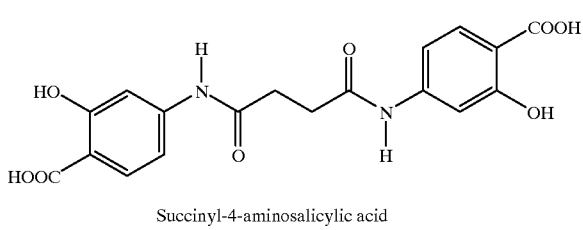
Succinyl-4-aminosalicylic acid
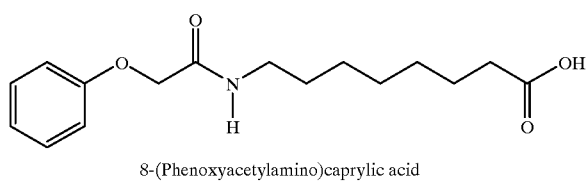
8-(Phenoxyacetylamino)caprylic acid
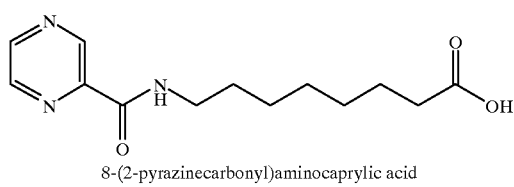
8-(2-pyrazinecarbonyl)aminocaprylic acid
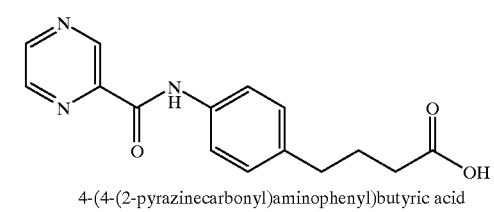
4-(4-(2-pyrazinecarbonyl)aminophenyl)butyric acid
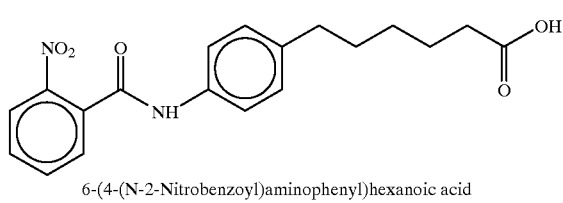
6-(4-(N-2-Nitrobenzoyl)aminophenyl)hexanoic acid -continued
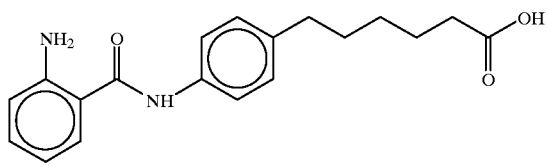
6-(4-(N-2-aminobenzoyl)aminophenyl)hexanoic acid
24
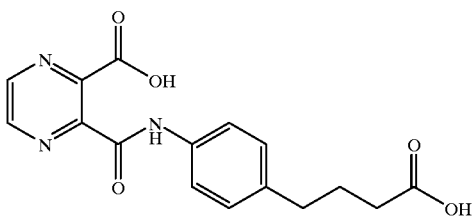
4-(4-(2-(3-carboxl)pyrazinecarboxyl)aminophenyl)butyric acid
25
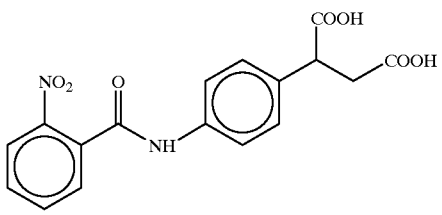
4-(2-Nitrobenzoyl)aminophenylsuccinic acid
26
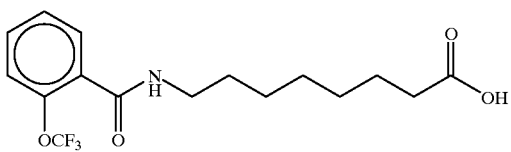
8-(2-(trifluoromethoxy)benzoyl)aminocaprylic acid
27
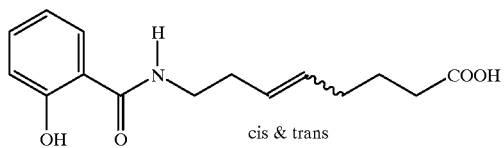
cis & trans
28
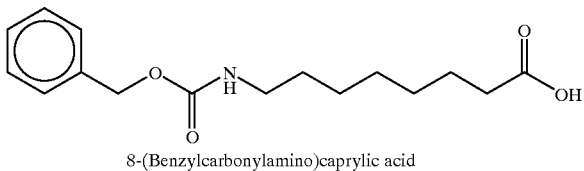
8-(Benzylcarbonylamino)caprylic acid
29
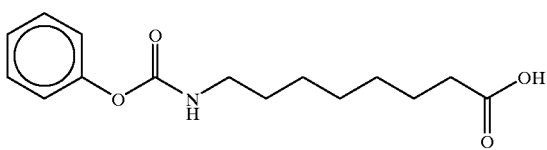
8(phenylcarbonylamino)caprylic acid
30

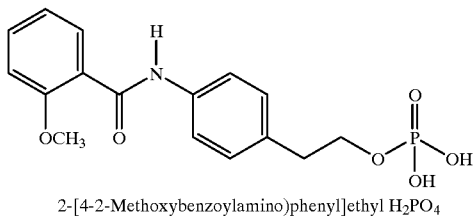
2-[4-2-Methoxybenzoylamino)phenyl]ethyl H₂PO₄
31
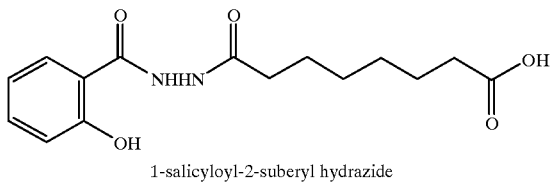
1-salicyloyl-2-suberyl hydrazide
32
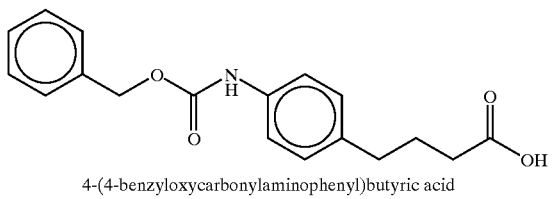
4-(4-benzyloxycarbonylaminophenyl)butyric acid
33
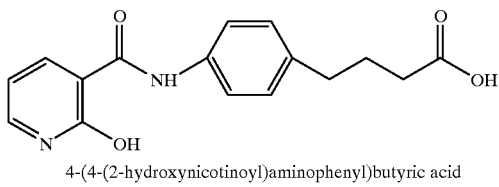
4-(4-(2-hydroxynicotinoyl)aminophenyl)butyric acid
34
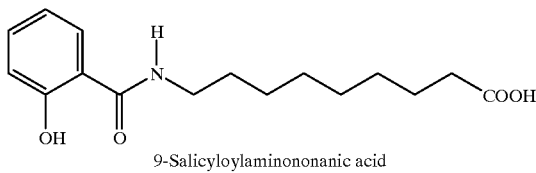
9-Salicyloylaminononanic acid
35
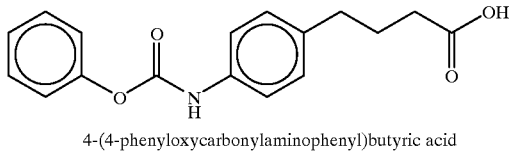
4-(4-phenyloxycarbonylaminophenyl)butyric acid
36
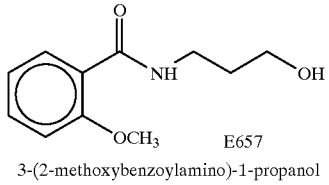
E657
3-(2-methoxybenzoylamino)-1-propanol
37
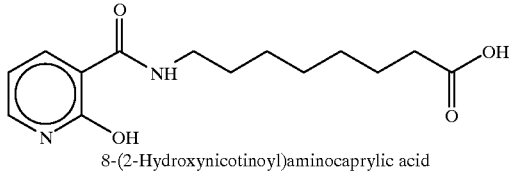
8-(2-Hydroxynicotinoyl)aminocaprylic acid
38

-continued
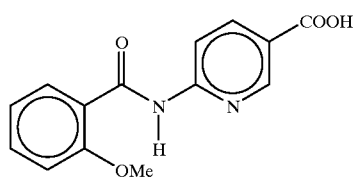
6-(2-methoxybenzoyl)amino nicotinic acid
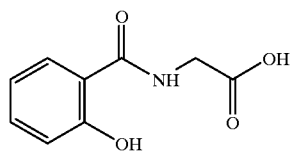
salicyloylglycine
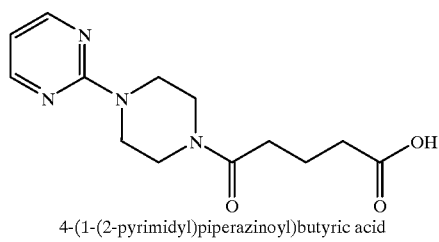
4-(1-(2-pyrimidyl)piperazinoyl)butyric acid
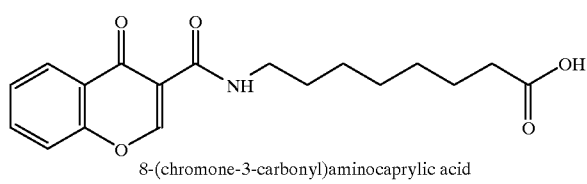
8-(chromone-3-carbonyl)aminocaprylic acid
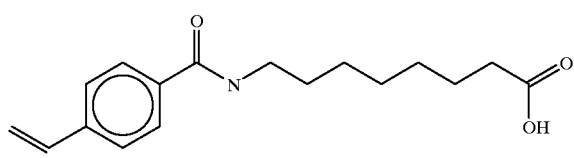
8-(vinylbenzoyl)aminocaprylic acid
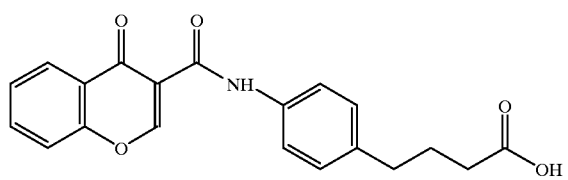
4-(4-(chromone-3-carbonyl)aminophenyl)butyric acid
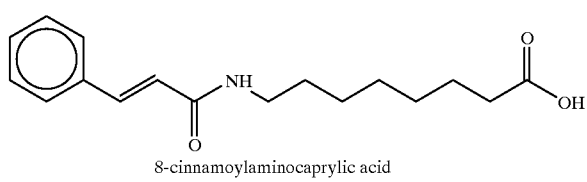
8-cinnamoylaminocaprylic acid

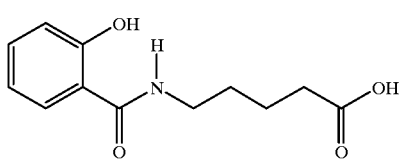
5-(N-salicyloylamino)valeric acid
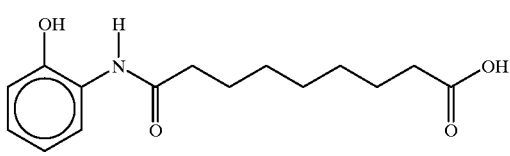
9-(2-hydroxybenzamido)nonanic acid
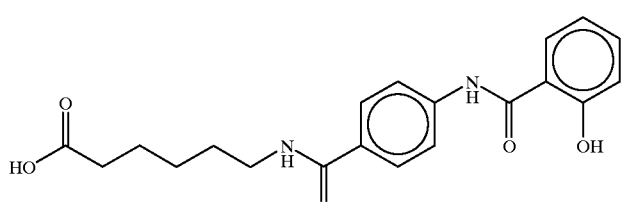
N-(4-salicyloylamino)-6-caproic acid
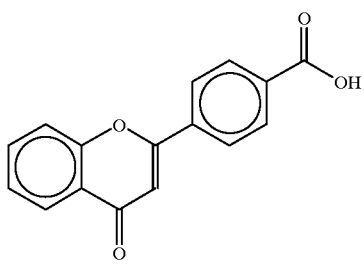
4'-flavonic acid
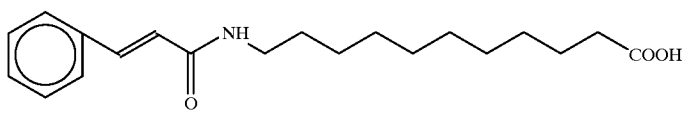
11-cinnamoylaminoundecanoic acid
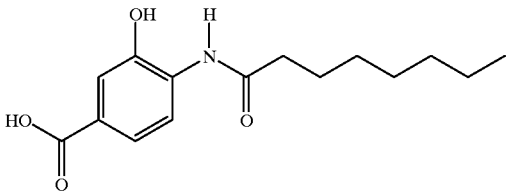
4-octanoylamino-3-hydroxybenzoic acid
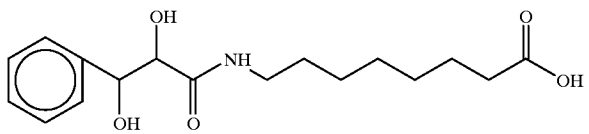
(3Phenyl2,3dihydroxypropanoyl)8aminocaprylic acid

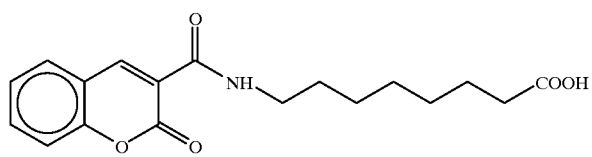
8-[N-(3-coumarincarbonyl)]aminocaprylic acid
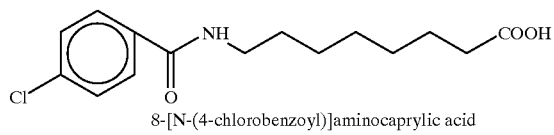
8-[N-(4-chlorobenzoyl)]aminocaprylic acid
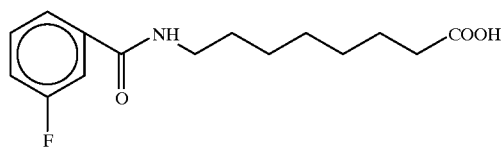
8-[N-3-fluorobenzoyl)]aminocaprylic acid
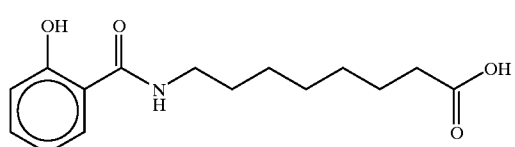
8-(N-2,5-Dihydroxybenzoyl)aminocaprylic acid
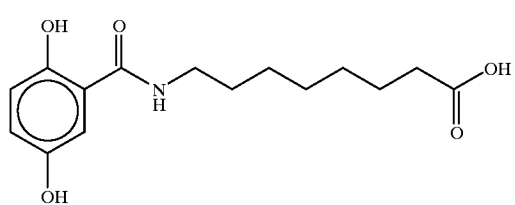
8-(N-2,3-Dimethoxybenzoyl)aminocaprylic acid
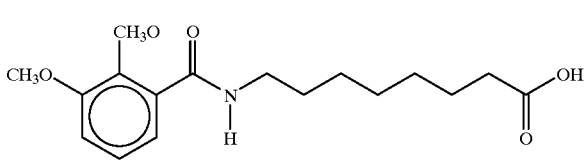
8-(N-2,4-Dihydroxybenzoyl)aminocaprylic acid
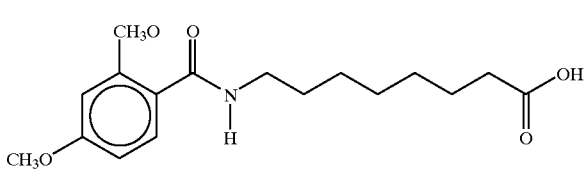
8-(N-2,5-Dimethoxybenzoyl)aminocaprylic acid

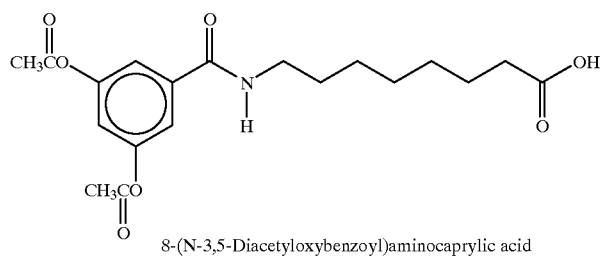
8-(N-3,5-Diacetyloxybenzoyl)aminocaprylic acid
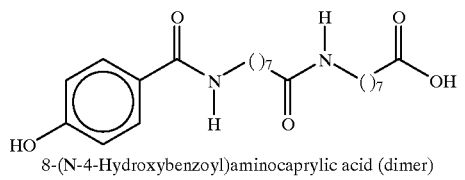
8-(N-4-Hydroxybenzoyl)aminocaprylic acid (dimer)
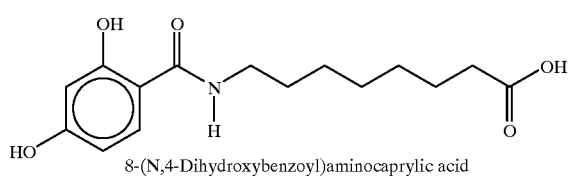
8-(N,4-Dihydroxybenzoyl)aminocaprylic acid
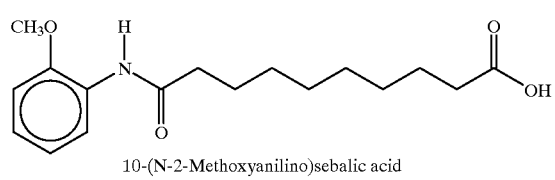
10-(N-2-Methoxyanilino)sebalic acid
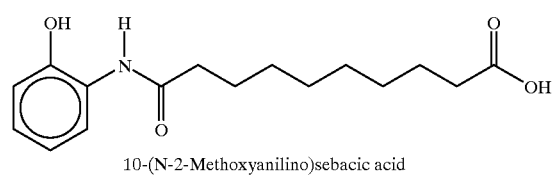
10-(N-2-Methoxyanilino)sebacic acid
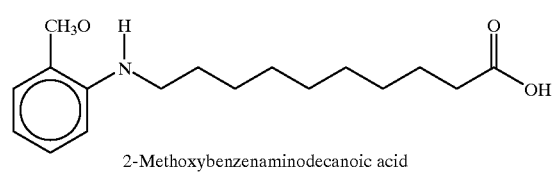
2-Methoxybenzenaminodecanoic acid
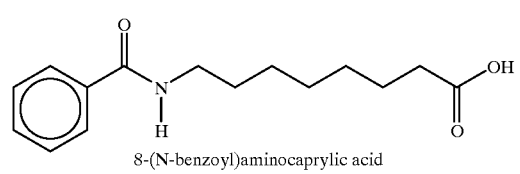
8-(N-benzoyl)aminocaprylic acid
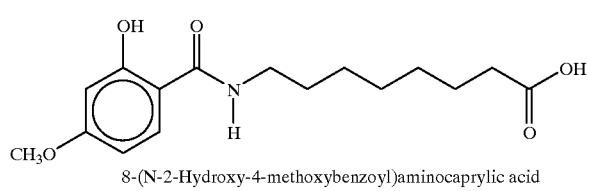
8-(N-2-Hydroxy-4-methoxybenzoyl)aminocaprylic acid -continued
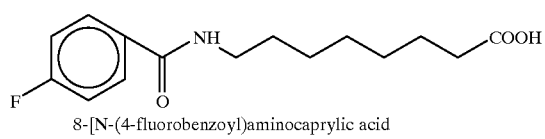
8-[N-(4-fluorobenzoyl)aminocaprylic acid
68
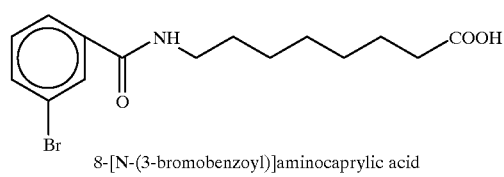
8-[N-(3-bromobenzoyl)]aminocaprylic acid
69
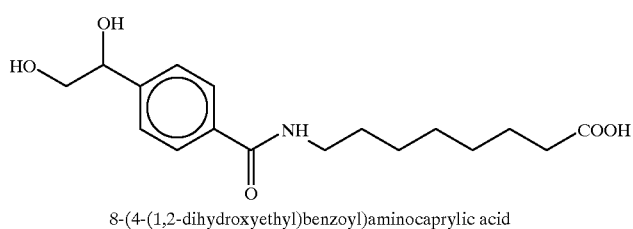
8-(4-(1,2-dihydroxyethyl)benzoyl)aminocaprylic acid
70
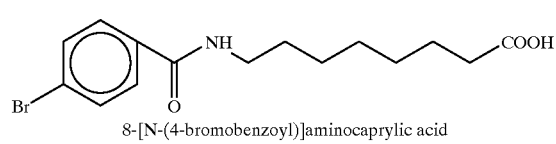
8-[N-(4-bromobenzoyl)]aminocaprylic acid
71
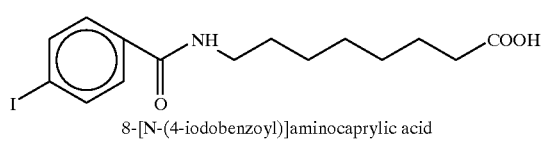
8-[N-(4-iodobenzoyl)]aminocaprylic acid
72
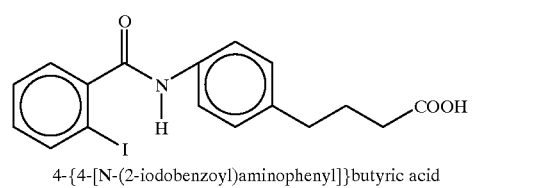
4-{4-[N-(2-iodobenzoyl)aminophenyl]}butyric acid
73
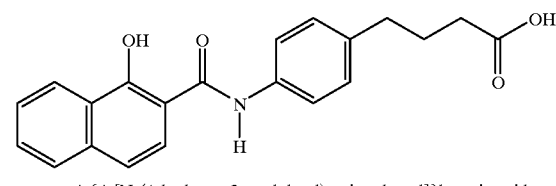
4-{4-[N-(1-hydroxy-2-naphthoyl)aminophenyl]}butyric acid
74
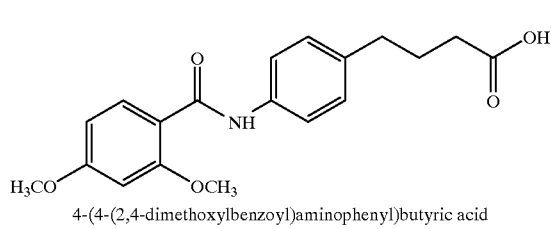
4-(4-(2,4-dimethoxylbenzoyl)aminophenyl)butyric acid
75

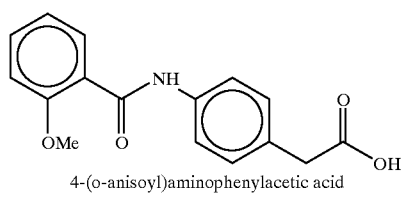
4-(o-anisoyl)aminophenylacetic acid
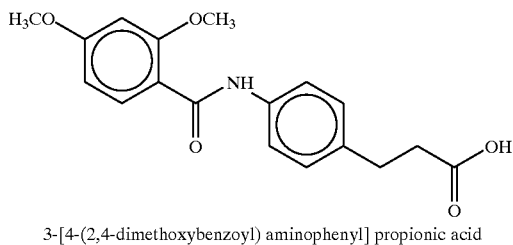
3-[4-(2,4-dimethoxybenzoyl) aminophenyl] propionic acid
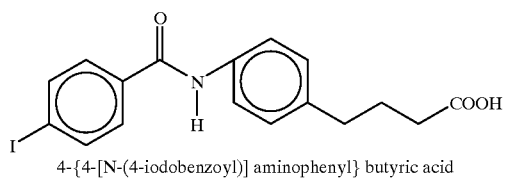
4-{4-[N-(4-iodobenzoyl)] aminophenyl} butyric acid
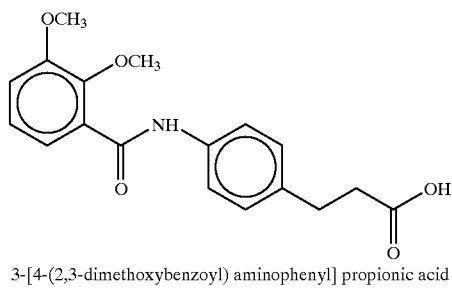
3-[4-(2,3-dimethoxybenzoyl) aminophenyl] propionic acid
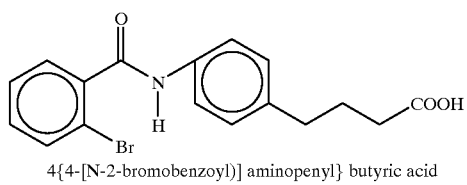
4{4-[N-2-bromobenzoyl)] aminopenyl} butyric acid
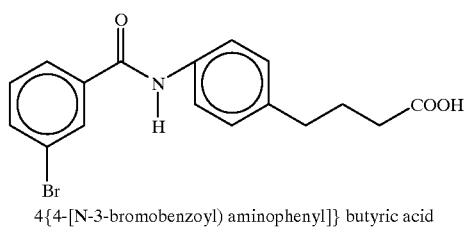
4{4-[N-3-bromobenzoyl) aminophenyl]} butyric acid
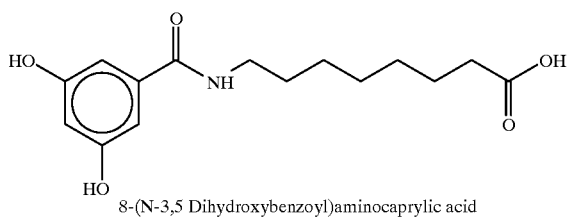
8-(N-3,5 Dihydroxybenzoyl)aminocaprylic acid

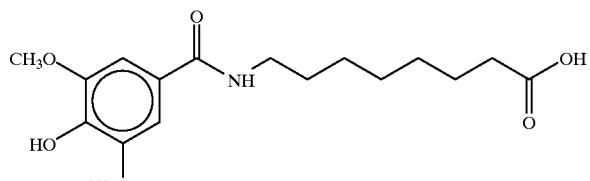
8-(N-3,5-Dimethoxy 4-hydroxybenzoyl)aminocaprylic acid
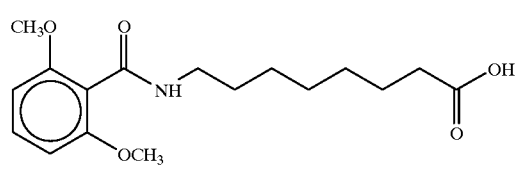
8-(N-2-6-Dimethoxybenzoyl)aminocaprylic acid
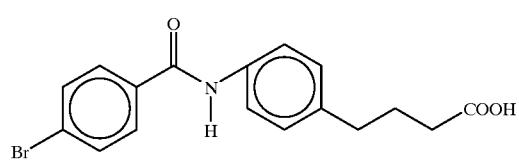
4-{4-[N-(4-bromobenzoyl)aminopenyl]}butyric acid
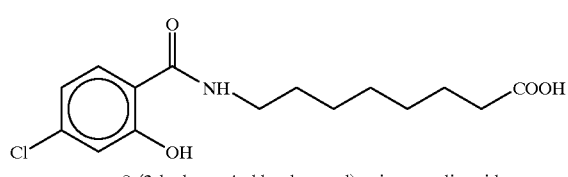
8-(2-hydroxy-4-chlorobenzoyl)aminocaprylic acid
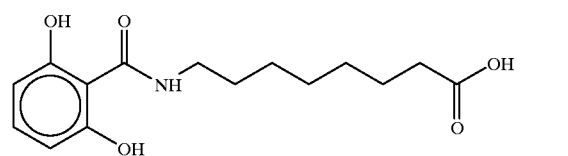
8-(N-2,6-Dihydroxybenzoyl)aminocaprylic acid
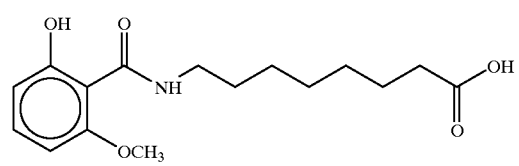
8-(N-2-Hydroxy6-methoxybenzoyl)aminocaprylic acid
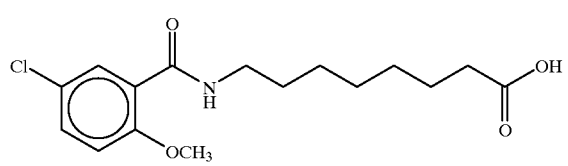
8-(5-chloro-o-anisoyl)aminocaprylic acid

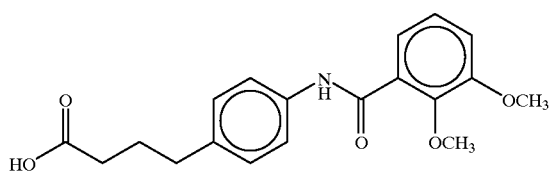
4-(4-(2,3-dimethoxybenzoyl)aminophenyl)butyric acid
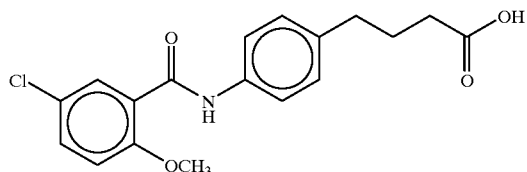
4-(4-(5-chloro-o-anisoyl)aminophenyl)butyric acid
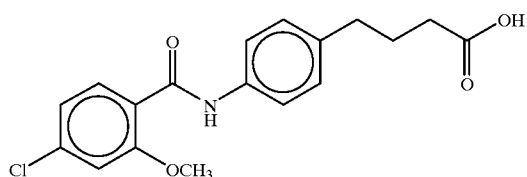
4-(4-(4-chloro-o-anisoyl)aminophenyl)butyric acid
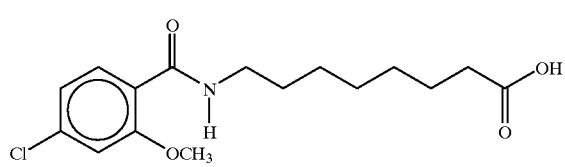
8-(4-chloro-o-anisoyl)aminocaprylic acid
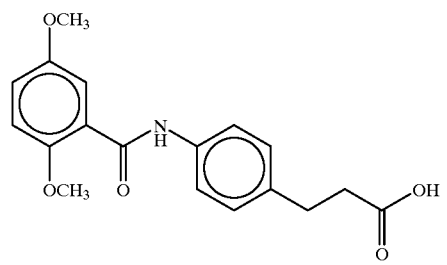
3-(4-(2,5-dimethoxybenzoyl)aminophenyl)propionic acid
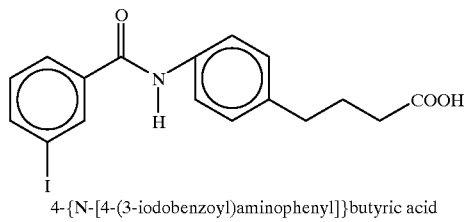
4-{N-[4-(3-iodobenzoyl)aminophenyl]}butyric acid
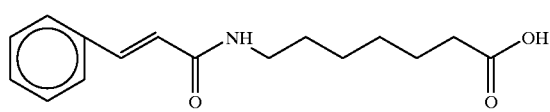
7-cinnamoylaminoheptanoic acid
90
91
92
93
94
95
96

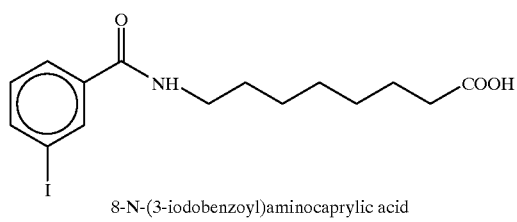
8-N-(3-iodobenzoyl)aminocaprylic acid
97
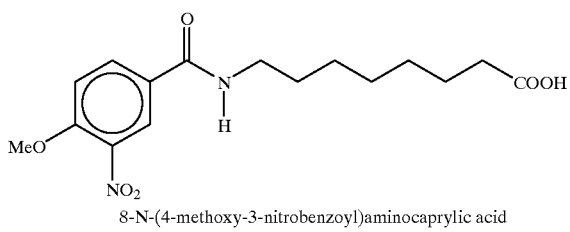
8-N-(4-methoxy-3-nitrobenzoyl)aminocaprylic acid
98
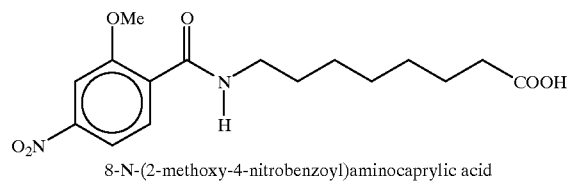
8-N-(2-methoxy-4-nitrobenzoyl)aminocaprylic acid
99
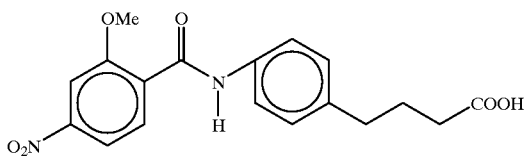
4-{N-[4-(2-methoxy-4-nitrobenzoyl)aminophenyl]}butyric acid
100
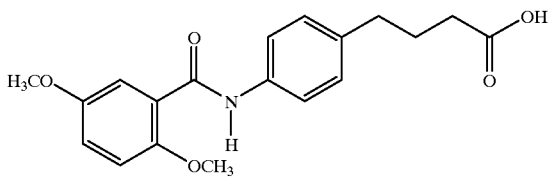
4-(4-(2,5-dimethoxybenzoyl)aminophenyl)butyric acid
101
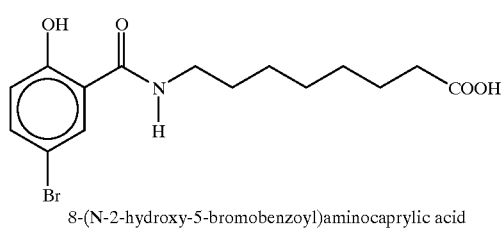
8-(N-2-hydroxy-5-bromobenzoyl)aminocaprylic acid
102
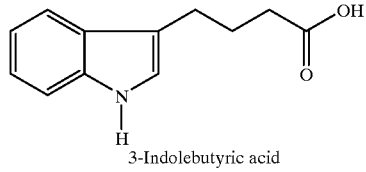
3-Indolebutyric acid
103

104
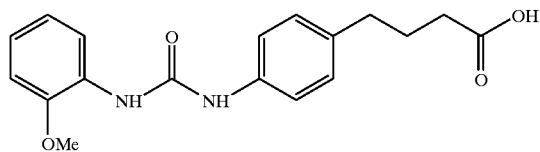
105
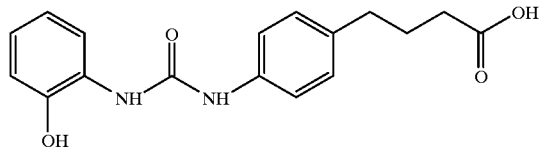
106
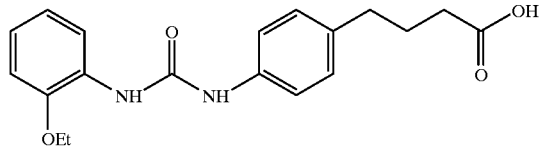
107
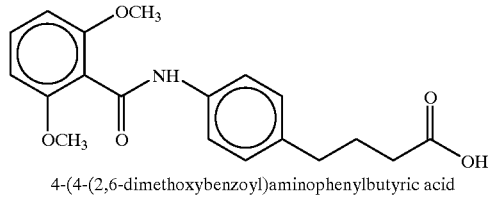
4-(4-(2,6-dimethoxybenzoyl)aminophenylbutyric acid
108
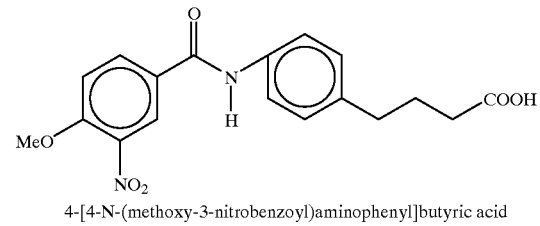
4-[4-N-(methoxy-3-nitrobenzoyl)aminophenyl]butyric acid
109
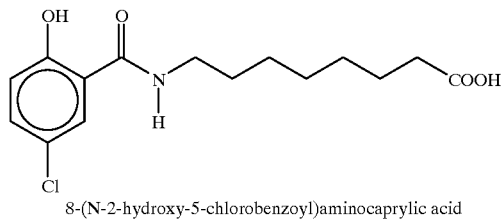
8-(N-2-hydroxy-5-chlorobenzoyl)aminocaprylic acid
110
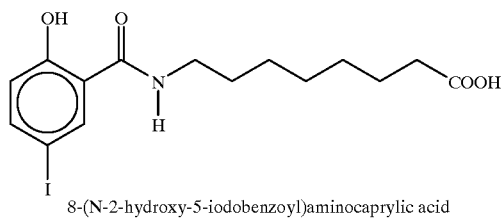
8-(N-2-hydroxy-5-iodobenzoyl)aminocaprylic acid

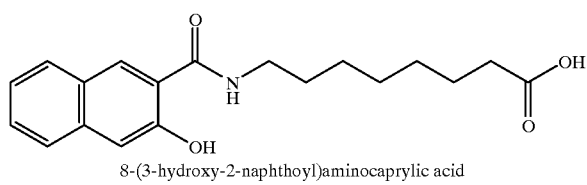
8-(3-hydroxy-2-naphthoyl)aminocaprylic acid
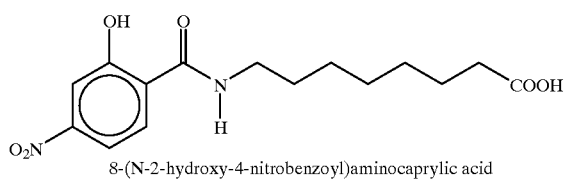
8-(N-2-hydroxy-4-nitrobenzoyl)aminocaprylic acid
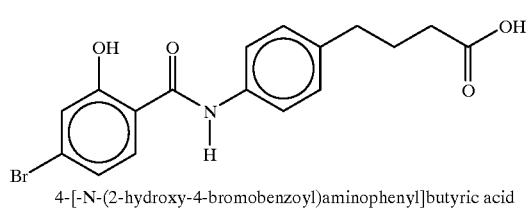
4-[-N-(2-hydroxy-4-bromobenzoyl)aminophenyl]butyric acid
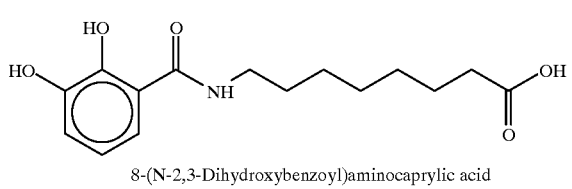
8-(N-2,3-Dihydroxybenzoyl)aminocaprylic acid
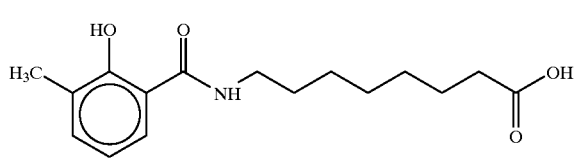
8-(N-3-methylsalicyloyl)aminocaprylic acid
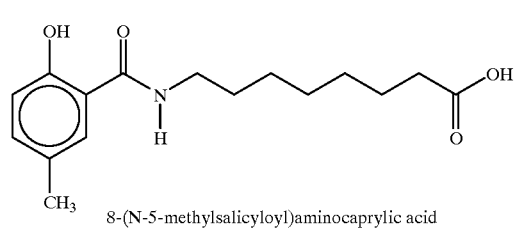
8-(N-5-methylsalicyloyl)aminocaprylic acid
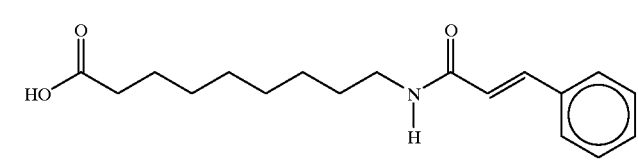
9-(cinnamoylamino)nonanoic acid
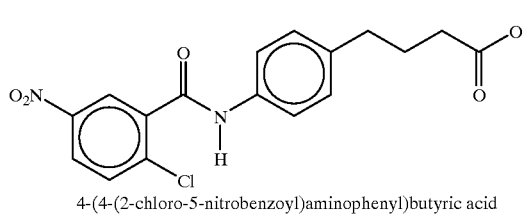
4-(4-(2-chloro-5-nitrobenzoyl)aminophenyl)butyric acid

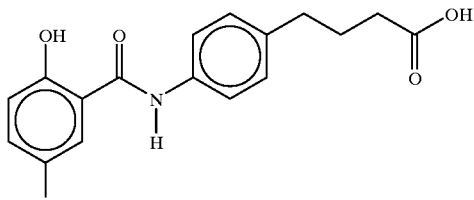
4-{-[N-(2-hydroxy-5-iodobenzoyl)]aminophenyl}butyric acid
119
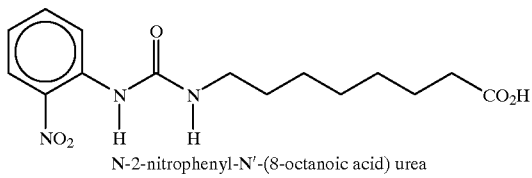
N-2-nitrophenyl-N'-(8-octanoic acid) urea
120
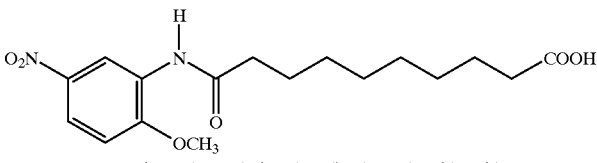
N-(2-methoxy-5-nitrophenyl) sebecoyl amide acid
121
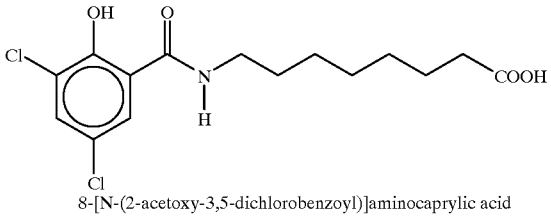
8-[N-(2-acetoxy-3,5-dichlorobenzoyl)]aminocaprylic acid
122
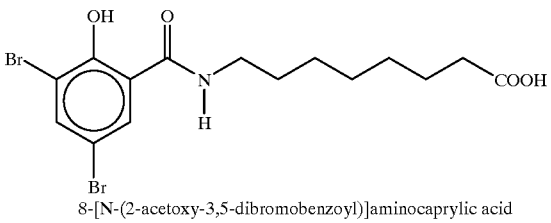
8-[N-(2-acetoxy-3,5-dibromobenzoyl)]aminocaprylic acid
123
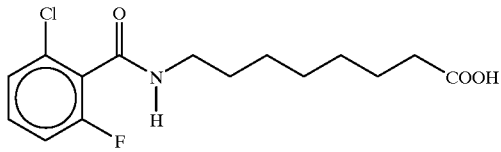
8-N-(2-chloro-6-fluorobenzoyl)aminocaprylic acid
124
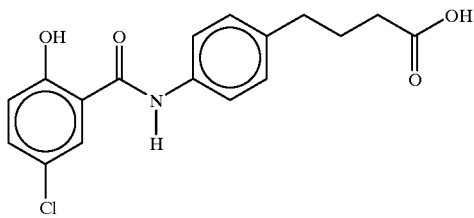
125

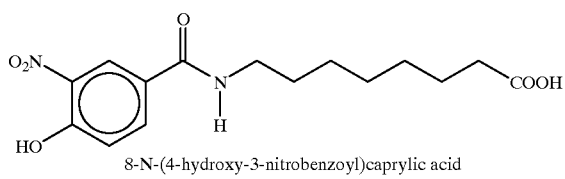
8-N-(4-hydroxy-3-nitrobenzoyl)caprylic acid
126
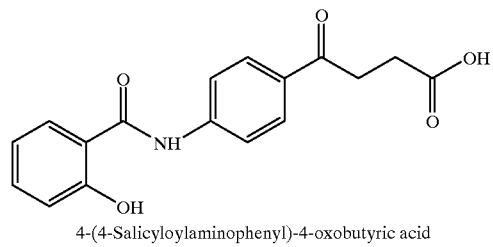
4-(4-Salicyloylaminophenyl)-4-oxobutyric acid
127
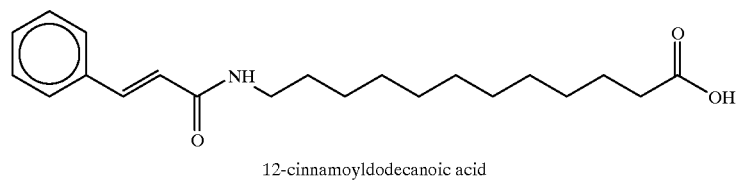
12-cinnamoyldodecanoic acid
128
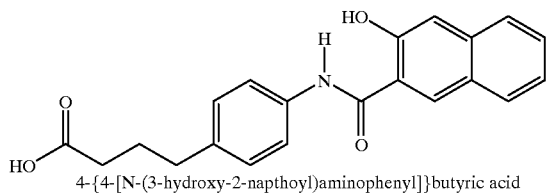
4-{4-[N-(3-hydroxy-2-napthoyl)aminophenyl]}butyric acid
129
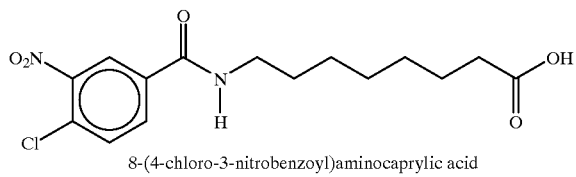
8-(4-chloro-3-nitrobenzoyl)aminocaprylic acid
130
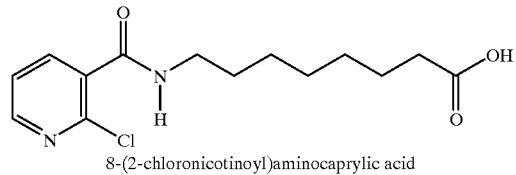
8-(2-chloronicotinoyl)aminocaprylic acid
131
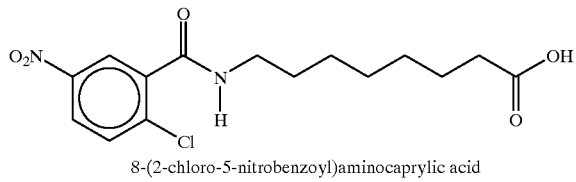
8-(2-chloro-5-nitrobenzoyl)aminocaprylic acid
132

-continued
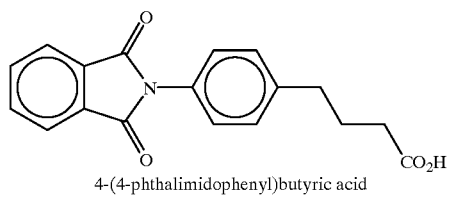
4-(4-phthalimidophenyl)butyric acid
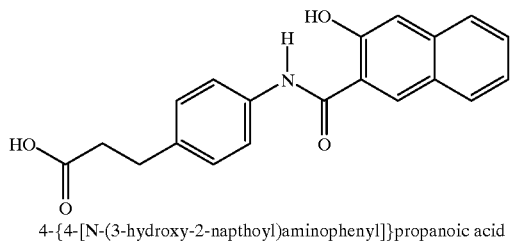
4-{4-[N-(3-hydroxy-2-napthoyl)aminophenyl]}propanoic acid
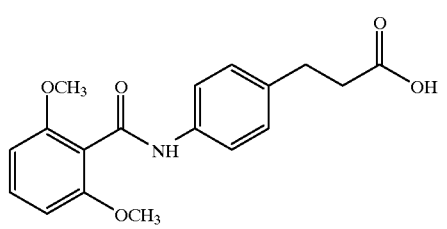
3-(4-(2,6-dimethoxybenzoyl)aminophenyl)propionic acid
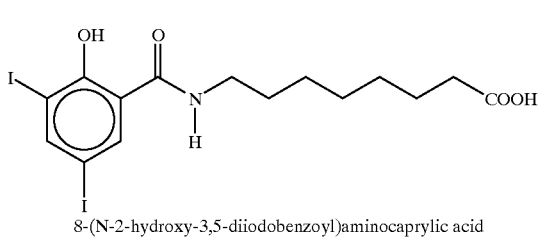
8-(N-2-hydroxy-3,5-diiodobenzoyl)aminocaprylic acid
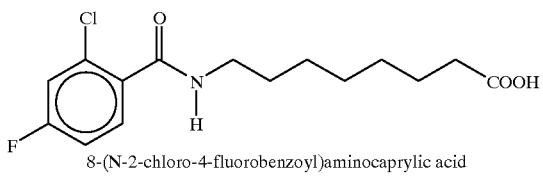
8-(N-2-chloro-4-fluorobenzoyl)aminocaprylic acid
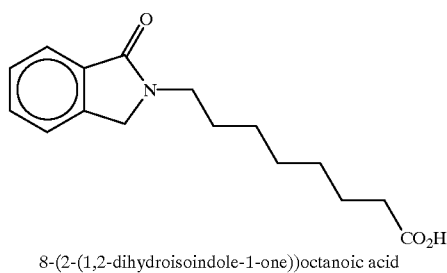
8-(2-(1,2-dihydroisoindole-1-one))octanoic acid
133
134
135
136
137
138

-continued
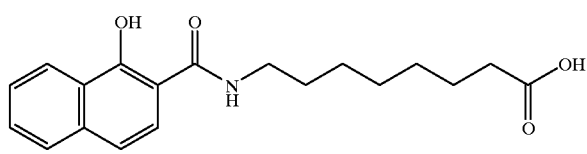
8-(N-1-hydroxy-2-naphthoyl)aminocaprylic acid
139
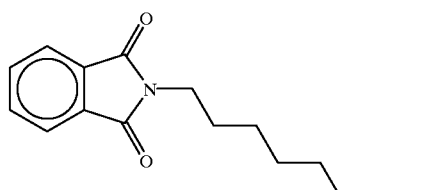
8-(phthalimido)caprylic acid
140
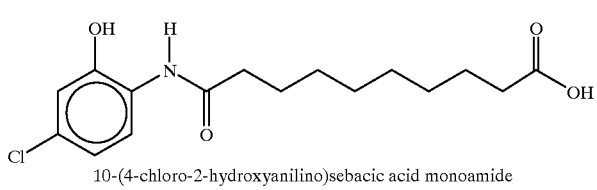
10-(4-chloro-2-hydroxyanilino)sebacic acid monoamide
141
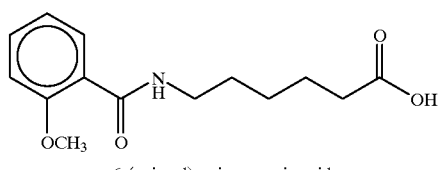
6-(anisoyl)aminocaproic acid
142
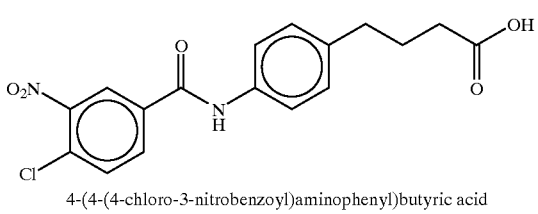
4-(4-(4-chloro-3-nitrobenzoyl)aminophenyl)butyric acid
143
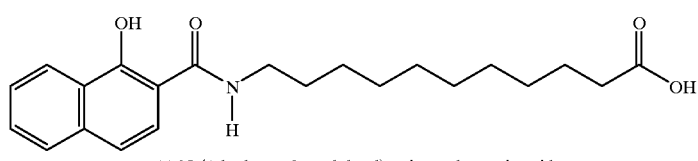
11-N-(1-hydroxy-2-naphthoyl)aminoundecanoic acid
144
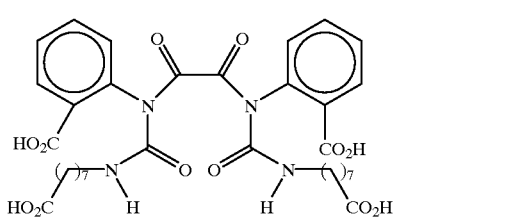
Bis(N-2carboxylphenyl-N-(N'-8-octanoic acid)ureal)oxalyl diamide
145

146
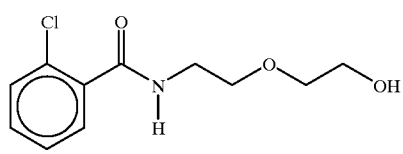
2-[2-N-(2-chlorobenzoyl)aminoethoxy]ethanol
147
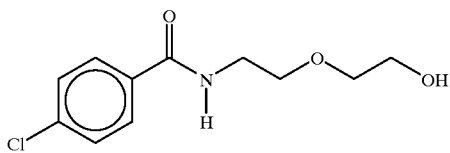
2-[2-N-(4-chlorobenzoyl)aminoethoxy]ethanol
148
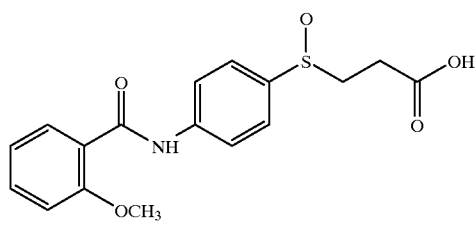
4-(2-methoxybenzoyl)amino 3-carboxysulfoxide
149
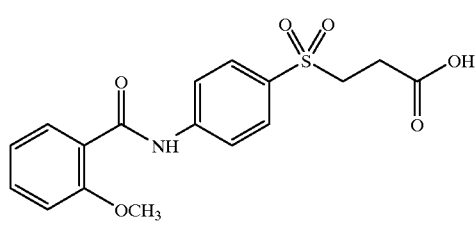
4-(2-methoxybenzoyl)amino 3-carboxypropylsulfone
150
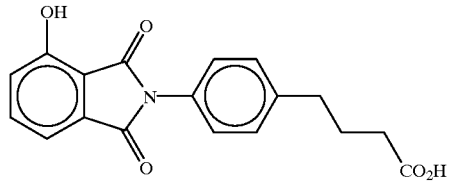
4-(4-(3-hydroxyphthalimido)phenyl)butyric acid
151
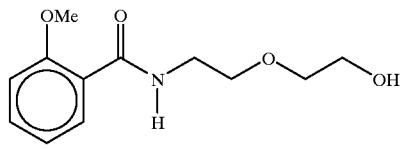
2-[2-N-(2-methoxybenzoyl)aminoethoxy)]ethanol
152
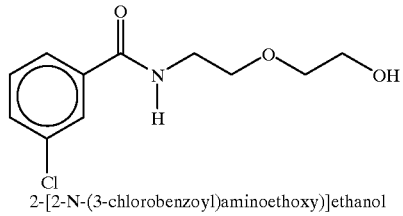
2-[2-N-(3-chlorobenzoyl)aminoethoxy)]ethanol 153
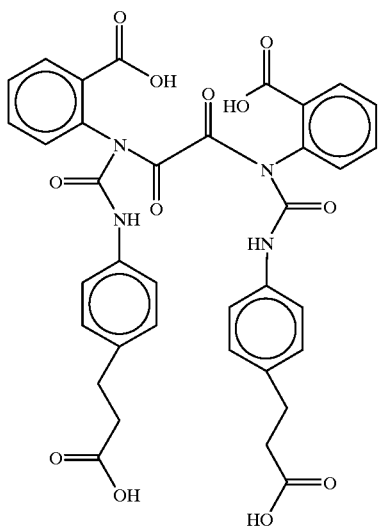
Bis(N-2-carboxyphenyl-N-(N'-3(4-aminophenyl)propionic acid)ureal)oxaylyl diamide
154
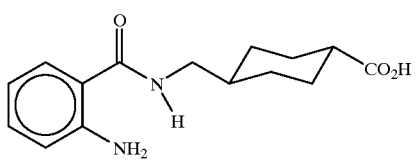
trans-4-(2-aminobenzamidomethyl)cyclohexamecarboxylic acid
155
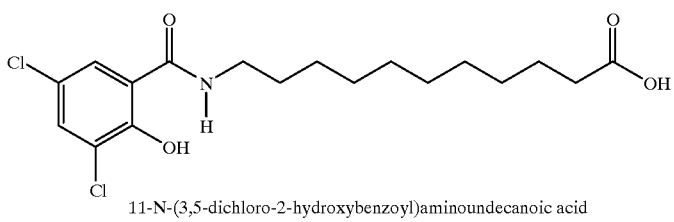
11-N-(3,5-dichloro-2-hydroxybenzoyl)aminoundecanoic acid
156
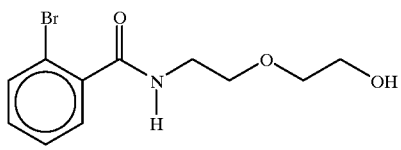
2-[N-(2-bromobenzoyl)aminoethoxy]ethanol
157
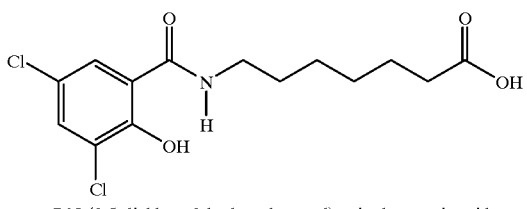
7-N-(3,5-dichloro-2-hydroxybenzoyl)aminoheptanoic acid

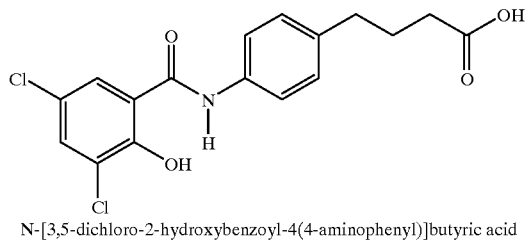
N-[3,5-dichloro-2-hydroxybenzoyl-4(4-aminophenyl)]butyric acid
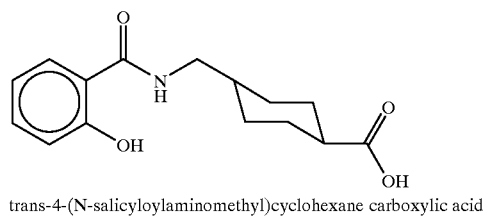
trans-4-(N-salicyloylaminomethyl)cyclohexane carboxylic acid
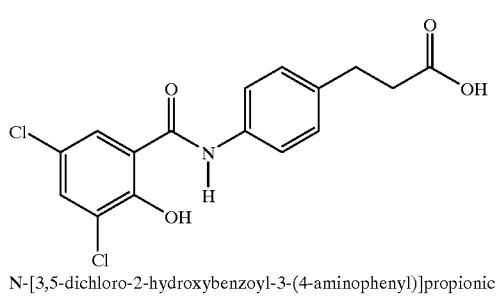
N-[3,5-dichloro-2-hydroxybenzoyl-3-(4-aminophenyl)]propionic acid
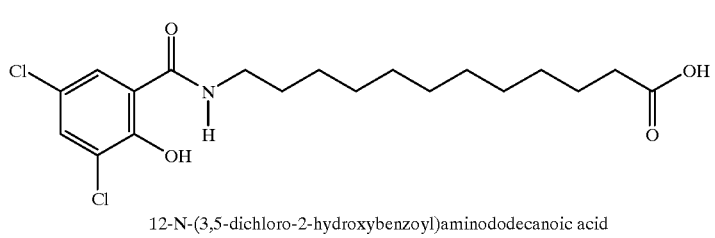
12-N-(3,5-dichloro-2-hydroxybenzoyl)aminododecanoic acid
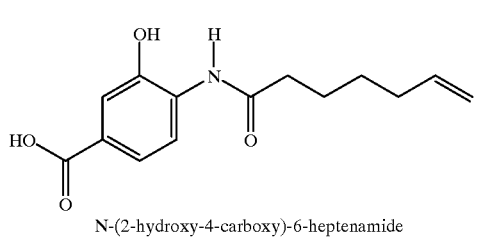
N-(2-hydroxy-4-carboxy)-6-heptenamide
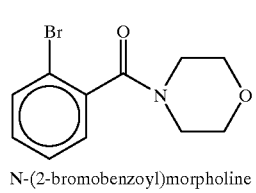
N-(2-bromobenzoyl)morpholine
158
159
160
161
162
163

164
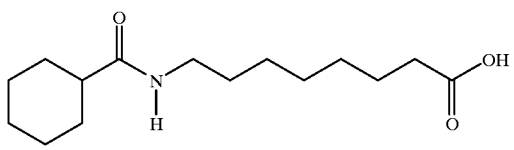
8-N-cyclohexanoylaminocaprylic acid
165
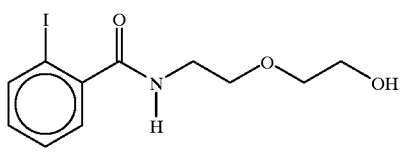
2-[N-(2-iodobenzoyl)aminoethoxy]ethanol
166
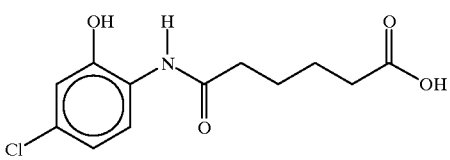
5-(4-chloro-2-hydroxyanilinocarbonyl)valeric acid
167
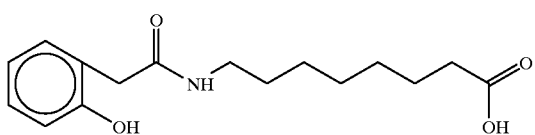
8-(2-hydroxyphenoxy)-aminocaprylic acid
168
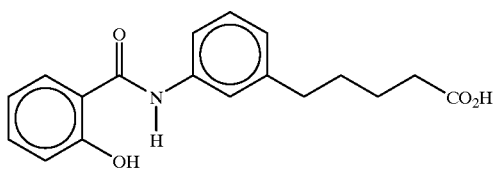
N-Salicoyl-5-(3-aminophenyl)valeric acid
169
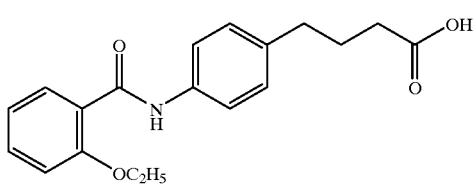
4-(4-(2-ethoxylbenzoyl)aminophenyl)butyric acid
170
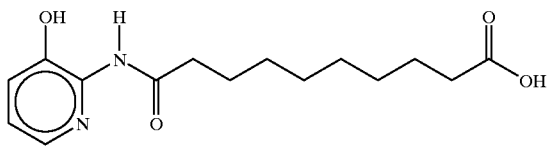
9-[2-(3-hydroxy)pyridylaminocarbonyl] nonanic acid
171
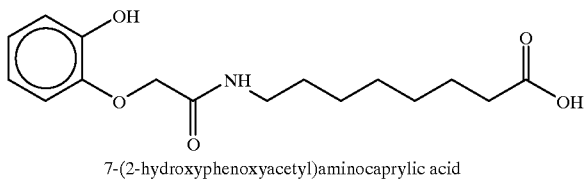
7-(2-hydroxyphenoxyacetyl)aminocaprylic acid

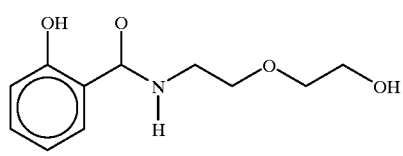
2-[N-(2-hydroxybenzoylamino)ethoxy]ethanol
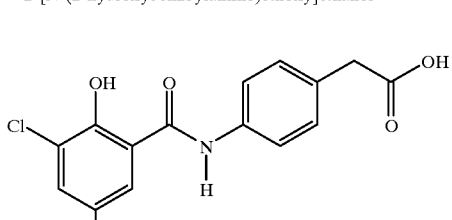
4-[N-(3,5-dichloro-2-hydroxybenzoyl)]aminophenylacetic acid
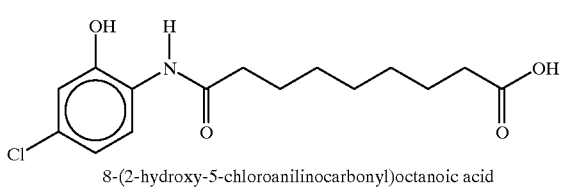
8-(2-hydroxy-5-chloroanilinocarbonyl)octanoic acid
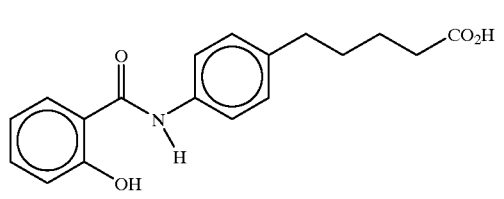
N-salicoyl-5-(4-aminophenyl)valeric acid
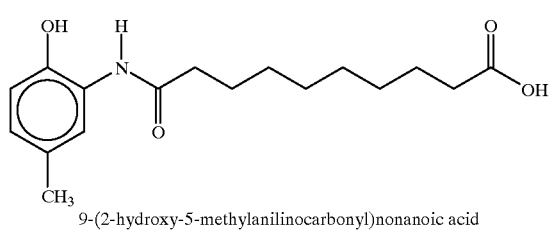
9-(2-hydroxy-5-methylanilinocarbonyl)nonanoic acid
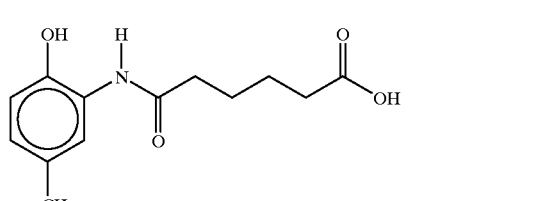
5-(2-hydroxy-5-methylanilinocarbonyl)valeric acid
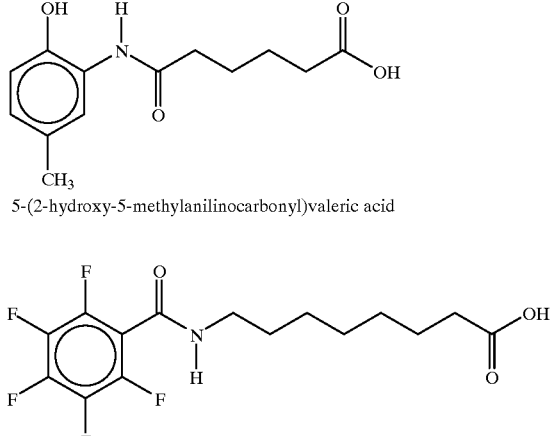
8-(pentafluorobenzoyl)aminocaprylic acid
172
173
174
175
176
177
178

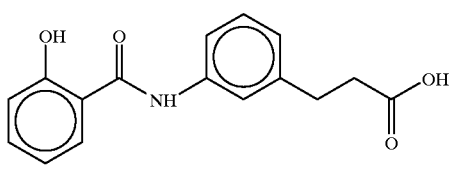
3-(3-(salicyloyl)aminophenyl)propionic acid
179
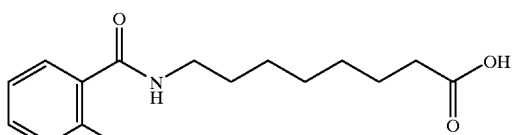
8-(2-ethoxybenzoyl)aminocaprylic acid
180
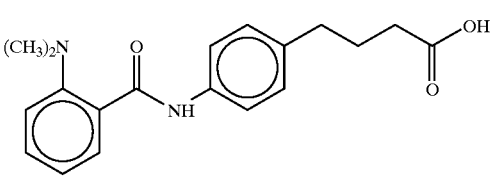
4-(4-(2-Dimethylamino benzoic)aminophenyl)butyric acid
181
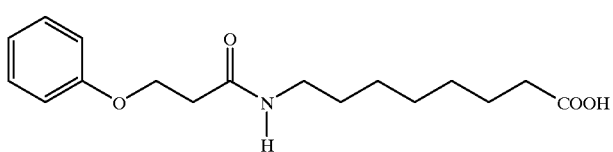
8-(3-Phenoxylpropionylamino)caprylic acid
182
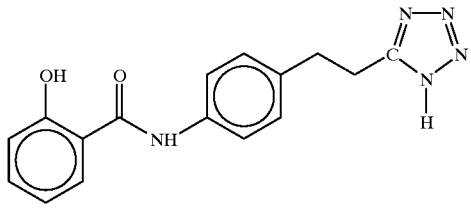
4-(Salicyloyl)aminophenylethyltetrazole
183
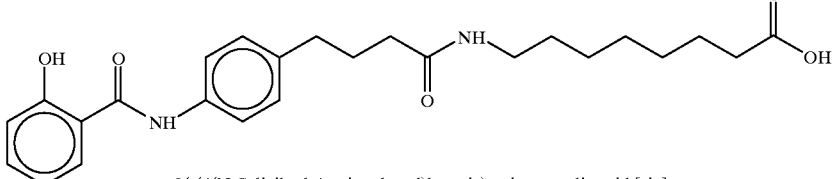
8(-(4(N-Saliciloyl-4aminophenyl)butyric)aminocaprylic acid [sic]
184
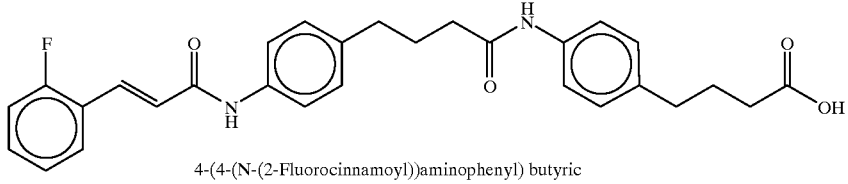
4-(4-(N-(2-Fluorocinnamoyl))aminophenyl) butyric
185

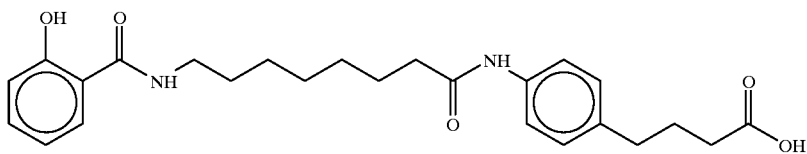
4-(4-(N-8(N-Salicyloyl)aminocaprylic)aminophenyl)butyric acid
186
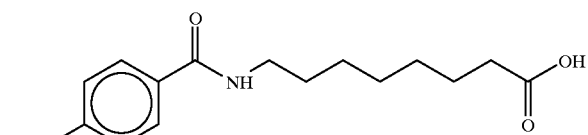
8-(p-anisoyl)aminocaprylic acid
187
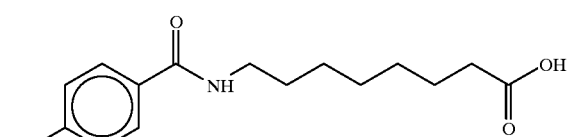
8-(4-Hydroxybenzoyl)aminocaprylic acid
188
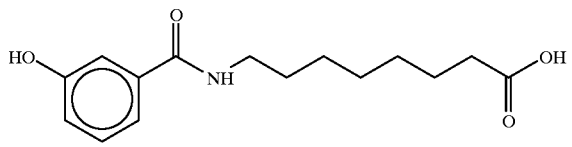
8-(3-Hydroxybenzoyl)aminocaprylic acid
189
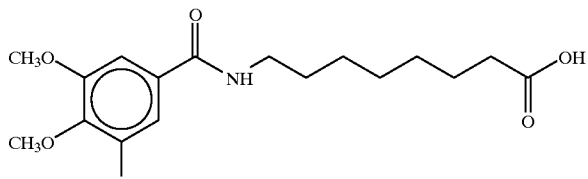
8-(3,4,5-Trimethoxybenzoyl)aminocaprylic acid
190
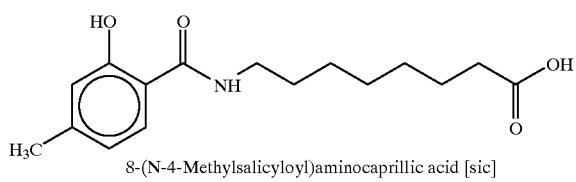
8-(N-4-Methylsalicyloyl)aminocaprillic acid [sic]
191
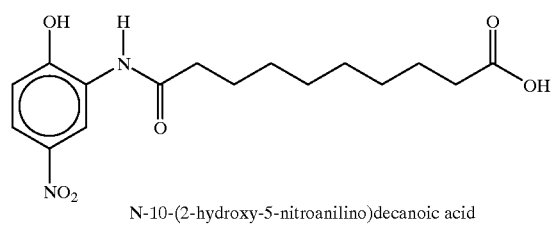
N-10-(2-hydroxy-5-nitroanilino)decanoic acid
192

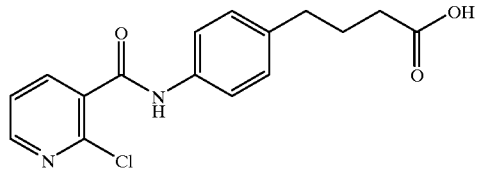

193

4-(4-(2-chloronicotinoyl)aminophenyl)butyric acid

Compositions comprising the carrier compounds discussed above and active agents are effective in delivering active agents to selected biological systems.

DETAILED DESCRIPTION OF THE INVENTION

The specific compositions of the present invention include an active agent and a carrier. These compositions may be used to deliver various active agents through various biological, chemical, and physical barriers and are particularly suited for delivering active agents which are subject to environmental degradation. The compositions of the subject invention are particularly useful for delivering or administering biologically or chemically active agents to any animals such as birds including, but not limited to, chickens; mammals, such as primates and particularly humans; and insects.

Other advantages of the present invention include the use of easy to prepare, inexpensive raw materials. The compositions and the formulation methods of the present invention are cost effective, simple to perform, and amenable to industrial scale up for commercial production.

Subcutaneous, sublingual, and intranasal coadministration of an active agent, such as, for example, recombinant human growth hormone (rhGH); salmon calcitonin; heparin, including, but not limited to, low molecular weight heparin; parathyroid hormone; and compounds in compositions as described herein result in an increased bioavailability of the active agent compared to administration of the active agent alone.

Active Agents

Active agents suitable for use in the present invention include biologically or chemically active agents, chemically active agents, including, but not limited to, fragrances, as well as other active agents such as, for example, cosmetics.

Biologically or chemically active agents include, but are not limited to, pesticides, pharmacological agents, and therapeutic agents. For example, biologically or chemically active agents suitable for use in the present invention include, but are not limited to, peptides, and particularly small peptides; hormones, and particularly hormones which by themselves do not or only a fraction of the administered dose passes through the gastro-intestinal mucosa and/or are susceptible to chemical cleavage by acids and enzymes in the gastro-intestinal tract; polysaccharides, and particularly mixtures of muco-polysaccharides; carbohydrates; lipids; or any combination thereof. Further examples include, but are not limited to, human growth hormones; bovine growth hormones; growth releasing hormones; interferons; interleukin-1; insulin; heparin, and particularly low molecular weight heparin; calcitonin; erythropoietin; atrial naturetic factor; antigens; monoclonal antibodies; somatostatin; adrenocorticotropin, gonadotropin releasing hormone; oxytocin; vasopressin; cromolyn sodium (sodium or disodium chromoglycate); vancomycin; desferrioxamine (DFO); parathyroid hormone anti-microbials, including, but not limited to anti-fungal agents; or any combination thereof.

Carriers

Although compounds 1–193 above have been found to act as carriers for the oral delivery of biologically or chemically active agents, special mention is made of compounds 9, 35, 64, 67, 79, 102, 109, 111, 117, 122, 136, and 141, above.

Properties of compounds 1–193 are listed in Table 1, below.

TABLE 1

| | Carrier Properties | | | | | | | | |
|---|---|---|---|---|---|---|---|---|---|
| | Anal. Calculated For | | | | Found | | | | Melting |
| Compound | C | H | N | S | C | H | N | S | Point (° C.) |
| 1 | 48.8 | 4.70 | 4.40 | | 48.81 | 4.64 | 4.39 | | |
| 2 | 64.73 | 7.97 | 10.06 | | 64.54 | 7.81 | 10.19 | | |
| 3 | 55.33 | 5.80 | 4.03 | | 55.40 | 5.79 | 3.96 | | 69–71 |
| 4 | 62.64 | 6.06 | 5.62 | | 62.75 | 6.08 | 5.51 | | 151–154 |
| 5 | 65.16 | 6.11 | 13.40 | | 65.29 | 6.03 | 13.29 | | 144–145 |
| 6 | 54.70 | 3.24 | 3.75 | | 54.29 | 3.24 | 3.54 | | 165–169 |
| 7 | 69.00 | 6.11 | 4.47 | | 69.09 | 6.24 | 4.43 | | 126–129 |
| 8 | 65.51 | 7.90 | 4.78 | | 65.60 | 8.25 | 4.83 | | 89–90 |
| 9 | 68.99 | 6.11 | 4.47 | | 69.01 | 6.08 | 4.47 | | 104–107 |
| 10 | 52.74 | 4.42 | 7.69 | | 52.91 | 4.45 | 7.49 | | 142–145 |
| 11 | 48.83 | 5.85 | 8.14 | | 48.95 | 5.89 | 8.02 | | 120–122 |
| 12 | 69.71 | 6.47 | 4.28 | | 69.56 | 6.47 | 4.38 | | 144–146 |
| 13 | 65.51 | 7.90 | 4.77 | | 65.23 | 7.88 | 4.72 | | 72.5–74.5 |

TABLE 1-continued

Carrier Properties

| Compound | Anal. Calculated For | | | | Found | | | | Melting Point (° C.) |
|---|---|---|---|---|---|---|---|---|---|
| | C | H | N | S | C | H | N | S | |
| 14 | 60.17 | 5.36 | 4.39 | 10.04 | 60.09 | 5.36 | 4.35 | 9.99 | 155–156 |
| 15 | 52.38 | 4.79 | 11.11 | | 52.45 | 4.94 | 11.08 | | 220–222 |
| 16 | 67.60 | 5.95 | 3.94 | | 67.34 | 6.01 | 3.91 | | 219–222 |
| 17 | 68.09 | 6.53 | 3.78 | | 67.77 | 6.24 | 3.81 | | 130–133 |
| 18 | 54.13 | 5.30 | 10.52 | | 54.12 | 5.24 | 10.54 | | 192.5–195.5 |
| 19 | 55.26 | 4.21 | 7.16 | | 54.48 | 4.32 | 6.86 | | >280 dec |
| 20 | 65.51 | 7.90 | 4.77 | | 65.52 | 7.90 | 4.77 | | 75–80 |
| 21 | 58.85 | 7.21 | 15.84 | | 58.86 | 7.16 | 15.69 | | 120–122 |
| 22 | 63.15 | 5.30 | 14.73 | | 63.30 | 5.43 | 14.18 | | 197–201 |
| 23 | 64.04 | 5.66 | 7.86 | | 64.17 | 5.67 | 7.75 | | 188–190 |
| 24 | 69.91 | 6.88 | 8.46 | | 69.98 | 6.79 | 8.58 | | 131–134 |
| 25 | 58.36 | 4.56 | 12.76 | | 58.20 | 4.63 | 12.61 | | 138–141 |
| 26 | 56.98 | 3.94 | 7.82 | | 56.39 | 3.92 | 7.74 | | 221–223 |
| 27 | 55.33 | 5.80 | 4.03 | | 55.47 | 6.10 | 4.04 | | 70–72 |
| 28 | | | | | | | | | |
| 29 | 65.74 | 7.58 | 4.79 | | 65.51 | 7.89 | 4.78 | | 52–55 |
| 30 | 64.50 | 7.57 | 5.02 | | 64.07 | 7.81 | 5.40 | | 70–74 |
| 31 | 54.70 | 5.17 | 3.99 | | 54.50 | 4.99 | 3.95 | | 173–174 |
| 32 | 58.63 | 5.94 | 9.12 | | 58.73 | 6.20 | 10.34 | | 125–129 |
| 33 | 69.00 | 6.10 | 4.47 | | 69.18 | 6.08 | 4.54 | | 100–102 |
| 34 | 63.99 | 5.37 | 9.33 | | 63.46 | 5.35 | 9.06 | | 218–221c |
| 35 | 65.5 | 7.90 | 4.78 | | 65.37 | 8.00 | 4.66 | | 96–97C |
| 36 | 68.22 | 5.72 | 4.68 | | 67.88 | 5.65 | 4.55 | | 134–137 |
| 37 | 63.14 | 7.23 | 6.69 | | 63.15 | 7.29 | 6.58 | | 53.5–56 |
| 38 | 60.00 | 7.14 | 10.00 | | 59.78 | 7.31 | 9.94 | | 135–138 |
| 39 | 61.67 | 4.41 | 10.29 | | 61.69 | 4.41 | 10.12 | | >225 |
| 40 | 55.39 | 4.65 | 7.18 | | 55.52 | 4.77 | 7.30 | | 162.5–166 |
| 41 | 56.10 | 6.52 | 20.14 | | 55.66 | 6.71 | 19.69 | | 129–131 |
| 42 | 65.24 | 6.39 | 4.23 | | 65.42 | 6.16 | 3.78 | | 130–133.5 |
| 43 | 70.59 | 7.96 | 4.84 | | 70.35 | 8.13 | 4.79 | | 111–113 |
| 44 | 68.37 | 4.88 | 3.99 | | 68.61 | 4.89 | 3.79 | | 120–123 |
| 45 | 70.59 | 7.96 | 4.84 | | 70.48 | 7.97 | 4.71 | | 108–110 |
| 46 | 60.75 | 6.37 | 5.90 | | 60.97 | 6.18 | 5.80 | | 100.5–103 |
| 47 | 64.50 | 7.57 | 5.02 | | 64.42 | 7.58 | 5.01 | | 97–100 |
| 48 | 64.86 | 5.98 | 7.56 | | 64.50 | 6.01 | 7.52 | | 165–169 |
| 49 | 72.18 | 3.76 | 0.00 | | 72.13 | 3.84 | 0.00 | | >225 |
| 50 | 72.51 | 8.76 | 4.23 | | 72.39 | 8.84 | 4.12 | | 120–122 |
| 51 | 64.50 | 7.58 | 5.01 | | 64.75 | 7.65 | 4.69 | | 200.5–204 |
| 52 | | 7.74 | 4.33 | | | 7.82 | 4.30 | | 88–89 |
| 53 | 65.24 | 6.39 | 4.23 | | 65.15 | 6.46 | 4.23 | | 93–97 |
| 54 | 60.49 | 6.77 | 4.70 | | 60.54 | 6.76 | 4.65 | | 114–116 |
| 55 | 64.04 | 7.17 | 4.98 | | 63.90 | 7.11 | 4.93 | | 105–106 |
| 56 | 61.00 | 7.17 | 4.74 | | 60.49 | 6.92 | 4.65 | | 146–148 |
| 57 | 63.14 | 7.79 | 4.33 | | 63.22 | 7.82 | 4.36 | | 59–61 |
| 58 | 63.14 | 7.79 | 4.33 | | 63.17 | 7.86 | 4.26 | | 102–104 |
| 59 | 63.14 | 7.79 | 4.33 | | 63.35 | 7.68 | 4.20 | | 89–90 |
| 60 | 60.15 | 6.64 | 3.69 | | 59.84 | 6.66 | 3.64 | | 112–113 |
| 61 | 65.53 | 8.85 | 6.65 | | 65.34 | 8.73 | 6.67 | | 89–92 |
| 62 | 61.00 | 7.17 | 4.74 | | 60.94 | 7.12 | 4.49 | | 104–108 |
| 63 | 66.43 | 8.20 | 4.56 | | 66.29 | 8.23 | 4.36 | | 77–78 |
| 64 | 65.51 | 7.90 | 4.77 | | 65.52 | 8.06 | 4.54 | | 97–98 |
| 65 | 69.59 | 9.28 | 4.77 | | 69.64 | 9.35 | 4.86 | | 62–65 |
| 66 | 68.41 | 8.04 | 5.32 | | 68.41 | 8.06 | 5.28 | | 88–89 |
| 67 | 62.12 | 7.49 | 4.53 | | 61.94 | 7.45 | 4.43 | | 98–99 |
| 68 | 64.04 | 7.17 | 4.98 | | 64.07 | 7.16 | 4.95 | | 106–107 |
| 69 | 52.64 | 5.89 | 4.09 | | 52.63 | 5.85 | 4.03 | | 109–110 |
| 70 | 63.15 | 7.74 | 4.33 | | 63.26 | 7.90 | 4.14 | | 97–100 |
| 71 | 52.64 | 5.89 | 4.09 | | 52.67 | 5.99 | 3.97 | | 114–115 |
| 72 | 46.31 | 5.18 | 3.61 | | 46.25 | 4.86 | 3.52 | | 143–144 |
| 73 | 49.89 | 3.94 | 3.42 | | 49.92 | 3.85 | 3.39 | | 170–171 |
| 74 | 72.19 | 5.48 | 4.01 | | 71.51 | 5.33 | 3.75 | | 180 |
| 75 | 66.46 | 6.16 | 4.08 | | 66.47 | 6.26 | 4.06 | | 168.5–171 |
| 76 | 67.37 | 5.26 | 4.91 | | 67.31 | 5.25 | 5.07 | | 130–133 |
| 77 | 65.65 | 5.78 | 4.26 | | 65.49 | 6.04 | 4.26 | | 179–183 |
| 78 | 49.89 | 3.94 | 3.42 | | 49.8 | 3.71 | 3.29 | | 237–238 |
| 79 | 65.65 | 5.78 | 4.26 | | 65.21 | 6.05 | 4.24 | | 156–158 |
| 80 | 56.38 | 4.45 | 3.87 | | 56.4 | 4.21 | 3.91 | | 130–131 |
| 81 | 56.38 | 4.45 | 3.87 | | 56.46 | 4.5 | 3.84 | | 197–198 |
| 82 | 56.6 | 7.49 | 4.4 | | 56.3 | 7.49 | 4.14 | | 58–62 |
| 83 | 57.03 | 8.2 | 3.91 | | 57.17 | 7.8 | 3.7 | | 138–140 |
| 84 | 57.58 | 7.11 | 3.95 | | 57.52 | 7.7 | 3.94 | | |
| 85 | 56.38 | 4.45 | 3.87 | | 56.31 | 4.25 | 3.64 | | 230–231 |
| 86 | 57.42 | 6.42 | 4.46 | | 57.14 | 6.45 | 4.2 | | 116–117 |

TABLE 1-continued

Carrier Properties

| Compound | Anal. Calculated For | | | | Found | | | | Melting Point (° C.) |
|---|---|---|---|---|---|---|---|---|---|
| | C | H | N | S | C | H | N | S | |
| 87 | 61 | 7.17 | 4.74 | | 61.18 | 7.05 | 4.65 | | 108–109 |
| 88 | 62.12 | 7.49 | 4.53 | | 62.34 | 7.21 | 4.39 | | 107–109 |
| 89 | 58.63 | 6.76 | 4.27 | | 58.53 | 6.81 | 4.2 | | 117–118 |
| 90 | 66.46 | 6.16 | 4.08 | | 66.18 | 6.15 | 3.84 | | 100–104 |
| 91 | 62.16 | 5.21 | 4.03 | | 61.93 | 4.97 | 3.86 | | 183–185 |
| 92 | 62.16 | 5.21 | 4.03 | | 62.2 | 5.14 | 3.98 | | 167–170 |
| 93 | 58.63 | 6.76 | 4.27 | | 58.64 | 6.83 | 4.19 | | 106–108 |
| 94 | 65.65 | 5.81 | 4.25 | | 65.56 | 5.64 | 4.2 | | 153–156 |
| 95 | 49.89 | 3.94 | 3.42 | | 49.9 | 3.81 | 3.18 | | 216–217 |
| 96 | 69.82 | 7.64 | 5.09 | | 69.91 | 7.66 | 5.02 | | 129–131 |
| 97 | 46.31 | 5.18 | 3.61 | | 46.54 | 4.95 | 3.64 | | 122–123 |
| 98 | 56.8 | 6.55 | 8.28 | | 56.69 | 6.67 | 8.1 | | |
| 99 | 56.8 | 6.55 | 8.28 | | 57.37 | 6.57 | 8.33 | | 117–118 |
| 100 | 60.33 | 5.06 | 7.82 | | 59.98 | 4.97 | 7.67 | | 207–209 |
| 101 | 66.46 | 6.16 | 4.08 | | 66.37 | 6.32 | 3.96 | | 126–128 |
| 102 | 50.29 | 5.63 | 3.91 | | 50.14 | 5.7 | 3.76 | | 129–131 |
| 103 | 70.93 | 5.95 | 6.89 | | 70.94 | 6.44 | 6.89 | | |
| 104 | 65.84 | 6.14 | 8.53 | | 65.94 | 6.19 | 8.54 | | 228–231 |
| 105 | 64.96 | 5.77 | 8.91 | | 64.89 | 5.82 | 8.82 | | |
| 106 | 66.65 | 6.48 | 8.18 | | 66.39 | 6.49 | 8.05 | | 140–142 |
| 107 | 66.47 | 6.12 | 4.07 | | 66.5 | 6.26 | 4.08 | | 140–142 |
| 108 | 60.33 | 5.06 | 7.82 | | 60.32 | 4.99 | 7.78 | | 150–151 |
| 109 | 57.41 | 6.42 | 4.46 | | 57.07 | 6.44 | 4.39 | | 121–123 |
| 110 | 44.46 | 4.97 | 3.46 | | | | | | 133–135 |
| 111 | 69.28 | 7.03 | 4.25 | | 68.86 | 7.07 | 4.11 | | 147–149 |
| 112 | 55.55 | 6.22 | 8.64 | | 55.27 | 5.99 | 8.5 | | 120–121 |
| 113 | 53.99 | 4.26 | 3.7 | | 53.98 | 4.25 | 3.63 | | 210 decom |
| 114 | 57.49 | 7.39 | 4.74 | | 57.72 | 7.57 | 4.43 | | 80–83 |
| 115 | 65.5 | 7.9 | 4.77 | | 64.97 | 7.79 | 4.75 | | 90–92 |
| 116 | 65.5 | 7.9 | 4.77 | | 65.11 | 8.03 | 4.71 | | 125–127 |
| 117 | 71.26 | 8.3 | 4.2 | | 70.6 | 7.89 | 4.83 | | 94–96 |
| 118 | 56.29 | 4.17 | 7.72 | | 56.23 | 4.01 | 7.6 | | 173–175 |
| 119 | 47.89 | 3.81 | 3.29 | | 47.52 | 3.71 | 3.16 | | 236–237 |
| 120 | 55.7 | 6.55 | 13 | | 55.71 | 6.58 | 13.05 | | 123–5 |
| 121 | 57.98 | 5.81 | 7.95 | | 57.9 | 7.11 | 7.82 | | 131–133 |
| 122 | 51.74 | 5.5 | 4.02 | | 51.41 | 5.43 | 3.61 | | 118–119.5 |
| 123 | 41.22 | 4.38 | 3.2 | | 41.45 | 4.36 | 2.94 | | 143–144.5 |
| 124 | 57.06 | 6.06 | 4.44 | | 57.02 | 6.12 | 4.35 | | 57–58 |
| 125 | 61.18 | 4.83 | 4.2 | | 60.71 | 4.76 | 3.89 | | 214 decom |
| 126 | 55.55 | 6.22 | 8.64 | | 55.4 | 6.24 | 8.53 | | 150–151 |
| 127 | 65.17 | 4.83 | 4.47 | | 65.27 | 4.87 | 4.48 | | 208–209 |
| 128 | 73.03 | 8.99 | 4.06 | | 72.92 | 9.36 | 4.1 | | 99–101 |
| 129 | 72.25 | 5.44 | 4 | | 72.14 | 5.24 | 4.01 | | 216–217 |
| 130 | 52.56 | 5.58 | 8.17 | | 52.66 | 5.44 | 8.21 | | 96–100 |
| 131 | 56.28 | 6.41 | 9.38 | | 56.32 | 6.42 | 9.28 | | 98–100 |
| 132 | 52.56 | 5.58 | 8.17 | | 52.46 | 5.65 | 7.86 | | 150–153 |
| 133 | 69.89 | 4.89 | 4.53 | | 69.64 | 5 | 4.54 | | 136–9 |
| 134 | 71.68 | 5.2 | 4.2 | | 71.24 | 5.1 | 4.13 | | 251–253 |
| 135 | 65.64 | 5.78 | 4.25 | | 65.3 | 5.91 | 4.04 | | 79–83 |
| 136 | 33.92 | 3.61 | 2.64 | | 34.48 | 3.84 | 2.48 | | 164–165 |
| 137 | 57.06 | 6.06 | 4.44 | | 57.09 | 6.17 | 4.45 | | 88–89 |
| 138 | 69.79 | 7.69 | 5.09 | | 69.68 | 7.78 | 5.08 | | 102–3 |
| 139 | 69.28 | 7.04 | 4.25 | | 68.99 | 7 | 4.1 | | 107–108 |
| 140 | 66.42 | 6.62 | 4.84 | | 66.2 | 6.49 | 4.81 | | 88–9 |
| 141 | 58.62 | 6.76 | 4.27 | | 58.66 | 6.93 | 4.18 | | 134–135 |
| 142 | 63.38 | 7.21 | 5.28 | | 63.22 | 7.28 | 5.24 | | 71–73 |
| 143 | 56.29 | 4.17 | 7.72 | | 56.19 | 4.04 | 7.65 | | 156–160 |
| 144 | 71.13 | 7.88 | 3.77 | | 70.39 | 7.91 | 3.64 | | 95–97 |
| 145 | 58.44 | 6.06 | 8.02 | | 58.25 | 6.38 | 7.84 | | 165–8 |
| 146 | 54.22 | 5.79 | 5.75 | | 54.26 | 5.65 | 5.69 | | 77–78.5 |
| 147 | 54.22 | 5.79 | 5.75 | | 54.21 | 5.85 | 5.61 | | 80–81 |
| 148 | 58.78 | 4.93 | 40.3 | | 58.64 | 4.89 | 3.97 | | 172–173 |
| 149 | 56.19 | 4.72 | 3.85 | | 56.31 | 4.67 | 3.86 | | 177 |
| 150 | 66.46 | 4.65 | 4.31 | | 66.41 | 4.56 | 4.23 | | 158–160 |
| 151 | 58.61 | 7.24 | 5.69 | | 58.79 | 7.35 | 5.66 | | |
| 152 | 54.22 | 5.79 | 5.75 | | 54.21 | 5.72 | 5.62 | | 54–55 |
| 153 | 60.85 | 4.25 | 7.89 | | 60.27 | 4.37 | 7.89 | | >260 |
| 154 | 62.5 | 7.3 | 10.14 | | 64.77 | 7.27 | 9.9 | | 187–190 |
| 155 | 55.4 | 6.5 | 3.6 | | 55.56 | 6.51 | 3.5 | | 114–116 |
| 156 | 45.85 | 4.9 | 4.86 | | 46.06 | 4.78 | 4.71 | | 67–68 |
| 156 | 48.8 | 4.7 | 4.4 | | 48.81 | 4.64 | 4.39 | | 144–146 |
| 157 | 50.3 | 5.1 | 4.2 | | 50.25 | 5.12 | 3.99 | | 141–143 |
| 158 | 55.5 | 4.1 | 3.8 | | 55.55 | 3.88 | 3.75 | | 190–192 |

TABLE 1-continued

Carrier Properties

| Compound | Anal. Calculated For | | | | Found | | | | Melting Point (° C.) |
|---|---|---|---|---|---|---|---|---|---|
| | C | H | N | S | C | H | N | S | |
| 159 | 64.97 | 6.9 | 5.05 | | 64.7 | 6.82 | 5.02 | | 171–174 |
| 160 | 54.3 | 3.7 | 4 | | 54.31 | 3.58 | 3.83 | | 222–224 |
| 161 | 56.4 | 6.7 | 3.5 | | 56.69 | 6.98 | 3.11 | | 76–78 |
| 162 | 63.63 | 6.47 | 5.3 | | 64.76 | 6.84 | 4.74 | | 188–191 |
| 163 | 48.91 | 4.48 | 5.19 | | 48.89 | 4.31 | 5.10 | | 88.5–90 |
| 164 | 66.66 | 10.04 | 5.18 | | 66.69 | 10.77 | 5.16 | | 67.5–70.5 |
| 165 | 39.42 | 4.21 | 4.18 | | 39.19 | 4.35 | 3.88 | | oil |
| 166 | 53.05 | 5.19 | 5.16 | | 53.06 | 5.03 | 4.86 | | 151–152 |
| 167 | 65.53 | 7.85 | 4.78 | | 65.4 | 7.84 | 4.57 | | 85–89 |
| 168 | 68.99 | 6.11 | 4.47 | | 68.62 | 5.87 | 4.49 | | 162–6 |
| 169 | 69.71 | 6.47 | 4.28 | | 69.67 | 6.58 | 4.50 | | 132.5–135 |
| 170 | 61.21 | 7.53 | 9.52 | | 61.21 | 7.68 | 9.46 | | 134–135 |
| 171 | 62.14 | 7.44 | 4.53 | | 61.96 | 7.52 | 4.57 | | 101–104 |
| 172 | 58.63 | 6.71 | 6.22 | | 58.15 | 6.83 | 6.04 | | |
| 173 | 52.96 | 3.26 | 4.12 | | 52.96 | 3.28 | 4.02 | | 225–227 |
| 174 | 57.42 | 6.42 | 4.46 | | 57.3 | 6.38 | 4.39 | | 119–120 |
| 175 | 68.99 | 6.11 | 4.47 | | 68.84 | 6.08 | 4.51 | | 131–4 |
| 176 | 66.43 | 8.2 | 4.56 | | 66.42 | 8.16 | 4.51 | | 109–110 |
| 177 | 62.14 | 6.82 | 5.57 | | 61.96 | 6.66 | 5.52 | | 127–128 |
| 178 | 51.00 | 4.56 | 3.97 | | 51.09 | 4.61 | 3.93 | | |
| 179 | 67.36 | 5.30 | 4.90 | | 67.26 | 5.24 | 4.91 | | 185–186 |
| 180 | 66.43 | 8.20 | 4.56 | | 66.32 | 8.60 | 5.12 | | 51.5–55 |
| 181 | 69.92 | 6.79 | 8.58 | | 67.02 | 6.93 | 8.20 | | 81–84 |
| 182 | 66.46 | 8.14 | 4.56 | | 66.43 | 8.34 | 4.47 | | 82–84 |
| 183 | 62.13 | 4.89 | 22.64 | | 62.05 | 4.88 | 22.45 | | 271–272 |
| 184 | 68.16 | 7.32 | 6.36 | | 67.73 | 7.44 | 6.70 | | 114–117 |
| 185 | 71.30 | 5.98 | 5.73 | | 71.10 | 5.97 | 5.74 | | 146–149 |
| 186 | 68.16 | 7.32 | 6.36 | | 67.94 | 7.31 | 6.41 | | 105–108 |
| 187 | 65.51 | 7.90 | 4.77 | | 65.35 | 7.63 | 4.59 | | 102–103 |
| 188 | 64.50 | 7.58 | 5.01 | | 64.19 | 7.69 | 4.83 | | 133–134 |
| 189 | 64.5 | 7.58 | 5.01 | | 64.5 | 7.57 | 4.90 | | 116–118 |
| 190 | 61.15 | 7.71 | 3.97 | | 61.27 | 7.79 | 4.08 | | 124–127 |
| 191 | 65.5 | 7.9 | 4.77 | | 65.32 | 7.94 | 4.7 | | 114–115 |
| 192 | 56.77 | 6.51 | 8.28 | | 56.83 | 6.76 | 8.21 | | 141–143 |
| 193 | 60.29 | 4.74 | 8.79 | | 60.17 | 4.58 | 8.74 | | 202–205 |
| 194 | 48.8 | 4.7 | 4.4 | | 48.81 | 4.64 | 4.39 | | 144–146 |

These carrier compounds or poly amino acids, and peptides, including the amino acids, may be used to deliver active agents including, but not limited to, biologically or chemically active agents such as for example, pharmacological and therapeutic agents.

An amino acid is any carboxylic acid having at least one free amine group and includes naturally occurring and synthetic amino acids.

Poly amino acids are either peptides or two or more amino acids linked by a bond formed by other groups which can be linked, e.g. an ester, anhydride, or an anhydride linkage.

Peptides are two or more amino acids joined by a peptide bond. Peptides can vary in length from dipeptides with two amino acids to poly peptides with several hundred amino acids. See *Chambers Biological Dictionary,* editor Peter M. B. Walker, Cambridge, England: Chambers Cambridge, 1989, page 215. Special mention is made of di-peptides, tri-peptides, tetra-peptides, and penta-peptides.

Salts such as, for example, sodium salt of these carrier compounds can be used as well.

Many of the compounds described herein are derived from amino acids.

Many of the compounds of the present invention can be readily prepared from amino acids including, but not limited to, aminocaprylic acid, butyrylhydroxaminic acid, aminophenylbutyric acid, aminophenylhexanoic acid, aminophenylpropionic acid, amino salicylic acid, aminophenylsuccinic acid, aminononanic acid, aminonicotinic acid, amino valenic acid, aminophenylacetic acid, aminocaproic acid, aminoundecanoic acid, aminoheptanoic acid, aminohydroxybenzoic acid, and aminodecanoic acid by methods within the skill of those in the art based upon the present disclosure and the methods described in U.S. patent application Ser. Nos. 60/017,902, filed Mar. 29, 1996; 08/414,654, filed Mar. 31, 1995; 08/335,148, filed Oct. 25, 1994; and 60/003,111, filed Sep. 1, 1995.

For example, these compounds may be prepared by reacting the single acid with the appropriate agent which reacts with free amino moiety present in the amino acids to form amides. Protecting groups may be used to avoid unwanted side reactions as would be known to those skilled in the art.

The carrier compound may be purified by recrystallization or by fractionation on solid column supports. Suitable recrystallization solvent systems include acetonitrile, methanol and tetrahydrofuran. Fractionation may be performed on a suitable solid column supports such as alumina, using methanol/n-propanol mixtures as the mobile phase; reverse phase column supports using trifluoroacetic acid/acetonitrile mixtures as the mobile phase; and ion exchange chromatography using water as the mobile phase. When anion exchange chromatography is performed, preferably a subsequent 0–500 mM sodium chloride gradient is employed.

Delivery Systems

The compositions of the present invention may include one or more active agents.

In one embodiment, compounds or salts of compounds 1–193 or poly amino acids or peptides that include at least one of these compounds or salts may be used directly as a delivery carrier by simply mixing one or more compound or salt, poly amino acid or peptide with the active agent prior to administration.

The administration mixtures are prepared by mixing an aqueous solution of the carrier with an aqueous solution of the active ingredient, just prior to administration. Alternatively, the carrier and the biologically or chemically active ingredient can be admixed during the manufacturing process. The solutions may optionally contain additives such as phosphate buffer salts, citric acid, acetic acid, gelatin, and gum acacia.

Stabilizing additives may be incorporated into the carrier solution. With some drugs, the presence of such additives promotes the stability and dispersibility of the agent in solution.

The stabilizing additives may be employed at a concentration ranging between about 0.1 and 5% (W/V), preferably about 0.5% (W/V). Suitable, but non-limiting, examples of stabilizing additives include gum acacia, gelatin, methyl cellulose, polyethylene glycol, carboxylic acids and salts thereof, and polylysine. The preferred stabilizing additives are gum acacia, gelatin and methyl cellulose.

The amount of active agent is an amount effective to accomplish the purpose of the particular active agent. The amount in the composition typically is a pharmacologically, biologically, therapeutically, or chemically effective amount. However, the amount can be less than a pharmacologically, biologically, therapeutically, or chemically effective amount when the composition is used in a dosage unit form, such as a capsule, a tablet or a liquid, because the dosage unit form may contain a multiplicity of carrier/biologically or chemically active agent compositions or may contain a divided pharmacologically, biologically, therapeutically, or chemically effective amount. The total effective amounts can then be administered in cumulative units containing, in total, pharmacologically, biologically, therapeutically or chemically active amounts of biologically or pharmacologically active agent.

The total amount of active agent, and particularly biologically or chemically active agent, to be used can be determined by those skilled in the art. However, it has surprisingly been found that with some biologically or chemically active agents, the use of the presently disclosed carriers provides extremely efficient delivery, particularly in oral, intranasal, sublingual, intraduodenal, or subcutaneous systems. Therefore, lower amounts of biologically or chemically active agent than those used in prior dosage unit forms or delivery systems can be administered to the subject, while still achieving the same blood levels and therapeutic effects.

The amount of carrier in the present composition is a delivery effective amount and can be determined for any particular carrier or biologically or chemically active agent by methods known to those skilled in the art.

Dosage unit forms can also include any of excipients; diluents; disintegrants; lubricants; plasticizers; colorants; and dosing vehicles, including, but not limited to water, 1,2-propane diol, ethanol, olive oil, or any combination thereof.

Administration of the present compositions or dosage unit forms preferably is oral or by intraduodenal injection.

The delivery compositions of the present invention may also include one or more enzyme inhibitors. Such enzyme inhibitors include, but are not limited to, compounds such as actinonin or epiactinonin and derivatives thereof. These compounds have the formulas below:

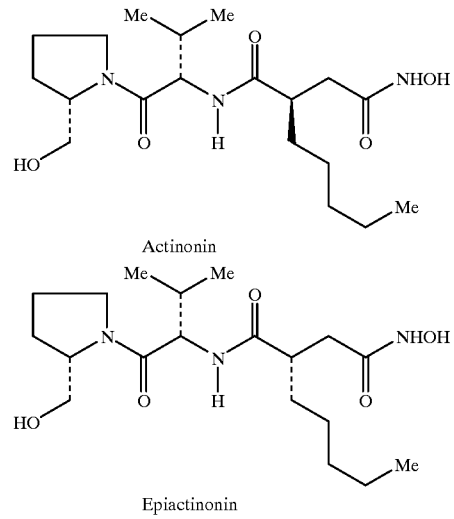

Actinonin

Epiactinonin

Derivatives of these compounds are disclosed in U.S. Pat. No. 5,206,384. Actinonin derivatives have the formula:

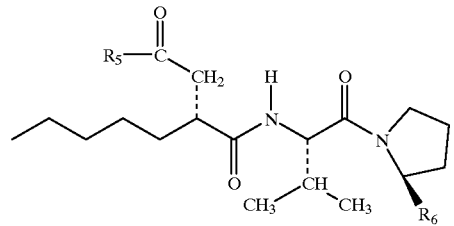

wherein $R^5$ is sulfoxymethyl or carboxyl or a substituted carboxy group selected from carboxamide, hydroxyaminocarbonyl and alkoxycarbonyl groups; and $R^6$ is hydroxyl, alkoxy, hydroxyamino or sulfoxyamino group. Other enzyme inhibitors include, but are not limited to, aprotinin (Trasylol) and Bowman-Birk inhibitor.

The compounds and compositions of the subject invention are useful for administering biologically or chemically active agents to any animals such as birds; mammals, such as primates and particularly humans; and insects. The system is particularly advantageous for delivering chemically or biologically or chemically active agents which would otherwise be destroyed or rendered less effective by conditions encountered before the active agent its target zone (i.e. the area in which the active agent of the delivery composition are to be released) and within the body of the animal to which they are administered. Particularly, the compounds and compositions of the present invention are useful in orally administering active agents, especially those which are not ordinarily orally deliverable.

DESCRIPTION OF THE PREFERRED EMBODIMENTS

The following examples illustrate the invention without limitation. All parts are given by weight unless otherwise indicated.

EXAMPLE 1

Carrier Preparation

General Preparations of Carriers. The following procedures were used to prepare the compounds described herein.

Many of the compounds were prepared by reaction of the appropriate amino acid with the appropriate acid chloride. The preparation of compound 79 is given as a representative example of the compounds prepared in this manner.

Preparation of Compound 79. Method A. A 1 L round bottom flask fitted with a magnetic stirrer was charged with 3-(4-aminophenyl)propionic acid (46.3 g, 0.28 moles, 1.17 equiv.) and 2 M aqueous sodium hydroxide (300 mL). 2,3-dimethoxybenzoylchloride (48.0 g, 0.24 moles, 1.00 equiv.) was added portionwise over 1 h to the stirred solution. After the addition, the reaction was stirred for 2.5 h at ambient temperature, and the pH of the solution was kept at ca 10 by the addition of 10 M sodium hydroxide. The solution was then acidified with 1 M hydrochloric acid (3×100 mL), water (100 mL), and air dried. It was redissolved in boiling acetone (ca 500 mL), decolorized with activated charcoal (3 g), and filtered. Water (1.5 L) was added to the filtrate to induce the formation of a brown oil. The brown oil solidified upon stirring at room temperature for 10 min. The crude solid was collected by filtration and recrystallized from 70% methanol-water (v/v) to afford compound 79 as a tan solid (39.5) g, 50%).

Compounds 1, 5, 30, 31, 33, 36, 53–66, 68, 69, 71–74, 78, 80–88, 95, 97–99, 102, 108–110, 112–115, 119, 121–126, 136, 137, 139, 141, 144, 146, 147, 151, 152, 155–158, 160, 161, 163, 165, 166, 170, 172–174, 176, 177, 184–186, 188, 189, 191 and 192 were also prepared by this process.

Preparation of Compound 79. Method B. A 2 L three-neck round bottom flask was fitted with a magnetic stirrer and two addition funnels under an argon atmosphere. A suspension of 3-(4-aminophenyl)propionic acid (46.3 g, 0.28 moles, 1.17 equiv.) in ethyl acetate (700 mL) was added to the flask. A solution of 2,3-dimethoxybenzoylchloride (48.0 g, 0.24 moles, 1.00 equiv.) in ethyl acetate (250 mL) was charged to one of the addition funnels and added dropwise over 1 h. Triethylamine (28.20 g, 0.28 moles, 1.00 equiv.) was subsequently charged to the second funnel and added dropwise over 15 min. The reaction was stirred at ambient temperature for 3 h, and the solvent was evaporated in vacuo giving a residual brown oil. Water (600 mL) was added to the residue followed by sodium hydroxide (2 M, 500 mL), and the mixture was stirred at ambient temperature for 3 hours. The resultant brown solution was acidified with 2 M hydrochloric acid (ca 1 L). After cooling the mixture in an ice bath for 1 h, a yellow solid formed and was collected by filtration. The solid was washed with water (3×1.5 L) and recrystallized from 50% ethanol-water (v/v) to give compound 79 as a tan solid (59.2 g, 68%).

Compounds 18, 32, 37, 41, 168, 175, and 183 were also prepared by this process.

Preparation of Compound 79. Method C. A 2 L round bottom flask equipped with a magnetic stirrer and a reflux condenser was charged with a suspension of 3-(4-aminophenyl)propionic acid (46.3 g, 0.28 moles, 1.17 equiv.) in dichloromethane (560 mL). Chlorotrimethylsilane (62.36 g, 0.57 moles, 2.05 equiv.) was added in one portion, and the mixture was heated to reflux for 1 h under argon. The reaction was allowed to cool to room temperature and was placed in an ice bath (internal temperature <10° C.). The reflux condenser was replaced with an addition funnel containing triethylamine (42.50 g, 0.42 moles, 1.50 equiv.). The triethylamine was added dropwise over 15 min, and a yellow solid formed during the addition. The funnel was replaced by another addition funnel containing a solution of 2,3-dimethoxybenzoylchloride (48.0 g, 0.24 moles, 1.00 equiv. in dichloromethane (100 mL). The solution was added dropwise over 30 min. The reaction was stirred in the ice bath for another 30 min and at ambient temperature for 1 h. The dichloromethane was evaporated in vacuo to give a brown oil. The brown oil was cooled in an ice bath, and an ice-cold solution of 2 M sodium hydroxide (700 mL) was added. The ice bath was removed, and the reaction was stirred for 2 h to afford a clear brown solution. The solution was acidified with 2 M sulfuric acid (400 mL) and stored at ca 5° C. for 1 hour. A yellow solid formed and was collected by filtration. The solid was washed with water (3×100 mL) and recrystallized from 50% ethanol-water (v/v) to afford compound 79 as tan needles (64.7 g, 82%).

Compounds 2–4, 6–17, 19–29, 34, 38–40, 42–48, 50–52, 67, 70, 75–77, 89–94, 96, 100, 101, 107, 111, 116–118, 127–132, 134, 135, 193, 142, 143, 148, 149, 159, 162, 164, 169, 178–182, 187, and 190 were also prepared by this process.

Preparation of Compound 35. A solution of O-acetylsalicyloyl chloride (24.68 g, 124 mmol, 1 equiv) in tetrahydrofuran (300 mL) was cooled in an ice bath. Triethylamine (25 g, 249 mmol, 2 equiv) was added dropwise via an additional funnel. The methyl 9-aminononanoate hydrochloride was dissolved in DMF (190 mL, slightly warm to dissolve), charged to an addition funnel and added dropwise to the above mixture. The reaction was stirred in the ice-bath for 20 min and at room temperature for 2 h. Evaporation of the THF under reduced pressure gave a pink DMF solution. The pink solution was cooled in an ice-bath, and 2 M aqueous sodium hydroxide (300 mL) was added. After being stirred at room temperature for 12 h, the mixture was acidified with 2 M hydrochloric acid (500 mL). The solution was cooled in an ice-bath, and a solid formed. The solid was collected by filtration and was recrystallized from 50% ethanol/water to give compound 35 (32 g, 87%) as an off-white solid.

Preparation of Compound 49. 1-(2-hydroxyphenyl)-3-(4-methyl benzoate)-1,3-propane dione (3.00 g, 0.0101 mil.) is placed in a 100 ml round bottomed flask fitted with argon purge, magnetic stir bar and cold water condenser. Glacial acetic acid (20 mls) and concentrated sulfuric acid (5 mls) were added, and heating of the reaction mixture was initiated. The reaction mixture was allowed to heat at reflux for 6 h before heating was discontinued. The reaction mixture was allowed to come to room temperature, and then was poured into 100 mls of ice/water. This was stirred for approximately ½ h before the mixture was filtered, and a brown solid was isolated. The brown solid was recrystallized twice from acetic acid, yielding compound 49 as a tan solid (1.44 g, 53.8%).

Preparation of Compound 167. 2-coumaranone (4.21 g, 0.0314 mol) was dissolved, with stirring, in acetonitrile (75 mls) in a 250 ml round bottomed flask fitted with a magnetic stir bar, argon purge and cold water condenser. Triethylamine (3.18 g, 0.0314 mol) and 8-aminocaprylic acid (5.00 g, 0.0314 mol) were added, and a tan slurry was formed. Heating was started, and the reaction mixture was allowed to reflux overnight. After heating overnight, thin layer chromatography of the reaction mixture (50% ethyl acetate/50% hexane) indicated that the reaction had gone to completion. Heating was stopped, the reaction mixture was allowed to cool to room temperature, and was concentrated in vacuo. The resulting residue was taken up in methylene chloride, and was washed with two, 100 ml portions of 1N hydrochloric acid solution. The methylene chloride layer was dried with sodium sulfate and was concentrated in vacuo. The resulting tan solid was allowed to dry in vacuo overnight, yielding compound 167 as a tan solid (8.35 g, 70.4%).

Preparation of Compound 171. 1,4-benzodioxan-2-one (3.93 g, 0.0262 mol) was dissolved, with stirring, in acetonitrile (70 mls) in a 250 ml round bottomed flask fitted with a magnetic stir bar, argon purge and cold water condenser. Triethylamine (2.64 g, 0.0262 mol) and 8-aminocaprylic acid (500 g, 0.0262 mol) were added and a tan slurry was formed. Heating was started, and the reaction mixture was allowed to reflux for approximately 3 hours. At this time, thin layer chromatography of the reaction mixture (50% ethyl acetate /50% hexane) indicated that the reaction had gone to completion. Heating was discontinued, and the reaction mixture was allowed to cool to room temperature and was concentrated in vacuo. The resulting residue was taken up in methylene chloride and was washed with a 100 ml portion of 1N hydrochloric acid solution. At this time, a tan solid was noted to precipitate, and it was isolated by filtration. This tan solid was washed further with an additional 100 ml portion of 1 N hydrochloric acid solution, and then with 100 ml of water. The resulting tan solid was allowed to dry in vacuo overnight yielding Compound 171 as a tan solid (7.73 g, 95.6%).

Preparation of Compound 120. A solution of 3.00 g (18.3 mmol) of 2-nitrophenylisocyanate and 5 mL of tetrahydrofuran was dropwise over 10 min to an ice bath-cooled solution of 2.08 g (13.1 mmol) of 8-aminocaprylic acid, 1.40 mL of 10 N NaOH and 40 mL of water. The reaction mixture was stirred an additional 30 min, warmed to 25° C. and treated with 3% HCl solution until the pH was 5. The yellow precipitate was filtered off and rinsed with 100 ml of water. The yellow solid was recrystallized in 2-propanol and water to give 3.7 g of compound 120 as pale yellow crystals.

Compounds 104–106 were also prepared by this procedure.

Preparation of Compound 133. A suspension of 2.40 g (16.3 mmol) and 2.80 g (15.6 mmol) of 4-(4aminophenyl) butyric acid in 20 mL of propylene glycol, 2.40 mL (1.74 g, 17.3 mmol) of triethylamine and 10 mg (0.08 mmol) of dimethylaminopyridine was heated to 140° C. The mixture became a clear solution after 5 min at 140° C. After stirring for 330 min, the reaction mixture was cooled to 25° C. and diluted with 20 mL of water. The solid phthalimide which had formed was filtered off. The filtrate was acidified with 3% HCl solution. The resulting solid was filtered off and was recrystallized from 2-propanol and water to give 0.62 g of compound 133 as a tan solid.

Preparation of Compound 138. A solution of 1.73 g (12.9 mmol) of phthalic dialdehyde, 2.04 g 8-aminocaprylic acid and 20 mL of acetic acid was heated to reflux for 10 min. The reaction mixture was cooled to 40° C., diluted with water and extracted with $CH_2Cl_2$ (2×20 mL). The organic phase was washed with water and brine, dried over $Na_2SO_4$ and evaporated. The residue was dissolved in ether and extracted with 2N NaOH. The layers were separated. The aqueous layer was made acidic with 3% HCl and extracted with $CH_2Cl_2$. The organic phase was dried over $Na_2SO_4$ and evaporated. The yellow residue was crystallized from acetonitrile and water to give 1.25 g of compound 138 as a yellow solid.

Preparation of Compound 140. A mixture of 1.40 g (9.48 mmol) of phthalic anhydride and 1.51 g (9.48 mmol) of 8-aminocaprylic acid was heated to 150° C. for 5 min. Upon cooling, 2.61 g of solid compound 140 was received.

Compound 150 was also prepared by this procedure.

Preparation of Compound 145. A suspension of 2.11 g (10.1 mmol) ethyl carbamoylanthranilic acid and 5 mL of $CH_2Cl_2$ was treated with 2.20 mL of oxalyl chloride. After stirring for 1 h the volatiles were stripped off. At that same time, a suspension of 1.60 g (10.1 mmol) of 8-aminocaprylic acid and 15 mL of $CH_2Cl_2$ was treated with 2.60 mL (2.23 g, 20.5 mmol) of TMSCI. This mixture was heated to reflux for 90 min, cooled in an ice bath and treated with 4.30 mL (3.12 g, 30.9 mmol) of triethylamine. Five min later, a slurry of the residue from the oxalyl chloride reaction in 20 mL of $CH_2Cl_2$ was added. The reaction mixture was warmed to 25° C. and stirred overnight. Upon acidification of the mixture with 3% HCl, a white solid formed. The solid was filtered off and recrystallized from EtOH and water to give 1.88 g of compound 145.

Compound 153 was also prepared by this procedure.

Preparation of Compound 154. A suspension of 4.02 g (25.6 mmol) of trans-4-aminomethylcyclohexane-carboxylic acid, 4.18 g (25.6 mmol) of isatoic anhydride, 20 mL of $CH_2Cl_2$, 20 mL of dioxane, and 4 mL of water was heated to reflux for 12 h. The solution was cooled to 25° C. and extracted with ether (4×20 mL). The organic layer was dried over $Na_2SO_4$ and concentrated. The resulting solid was recrystallized from EtOH and water to give 4.95 g of compound 154.

Compound 103 is available from Aldrich Chemical Company, Inc., Milwaukee, Wis.

EXAMPLE 2

Parathyroid Hormone Dosing Solutions

Intracolonic ("IC") dosing compositions containing 100 mg/kg of carrier and 25 μg/kg of parathyroid hormone in 25% aqueous propylene glycol or oral gavage "PO") dosing solution containing 400 mg/kg of carrier and 100 μg/kg of parathyroid hormone in water, were prepared with carriers 9, 33, 35, 77, 79, 109, 110, 123, 136, 141, and 169. The dosing solutions are designated P-carrier number-DS.

COMPARATIVE EXAMPLE 2A

Parathyroid Hormone Dosing Solutions

An intracolonic dosing composition containing 100 mg/kg of a carrier having the formula

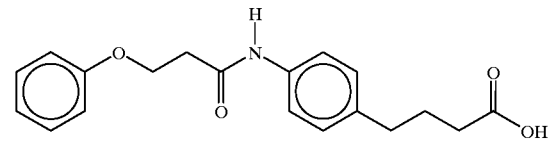

and 25 ug/kg of parathyroid hormone in 25% aqueous propylene glycol was prepared. The dosing solution is identified as P-9A-DS.

EXAMPLES 3

In vivo Parathyroid Hormone Delivery

Male Sprague-Dawley rats weighing between 200–250 g were fasted for 24 hours and were administered ketamine (44 mg/kg) and chlorpromazine (1.5 mg/kg) 15 minutes prior to dosing. The rats were administered one of dosing solutions P-9-DS, P-33-DS, P-35-DS, P-77-DS, P-79-DS, and P-141-DS by oral gavage ("PO") or intra-colonic instillation ("IC"). Blood samples were collected serially from the tail artery for serum determination of parathyroid hormone concentration. Serum parathyroid hormone concentrations were quantified by a parathyroid hormone immunoaccuracy test host.

Results are illustrated in Table 2, below.

COMPARATIVE EXAMPLE 3A

In vivo Parathyroid Hormone Delivery

The procedure of Example 3 was followed substituting dosing solution P-9A-DS for dosing solution P-9-DS. Results are illustrated in Table 2, below.

COMPARATIVE EXAMPLE 3B

In vivo Parathyroid Hormone Delivery

The procedure of Example 3 was followed with a dosing solution (at a dose of 25 µg/kg of parathyroid hormone (intra-colonic) or 100 µg/kg of parathyroid hormone (oral)), P-ØA-DS, that omitted the carrier.

Results are illustrated in Table 2, below.

TABLE 2

In vivo Parathyroid Hormone Delivery

| Dosing Solution | Mean Peak Serum [PTH] ± Standard Deviation (pg/ml) |
|---|---|
| P-9-DS | 155 ± 105 (IC) |
| P-33-DS | 58 ± 18 (IC) |
| P-35-DS | 50 ± 27 (IC) |
| P-77-DS | 358 ± 274 (PO) |
| P-79-DS | 521 ± 128 (PO) |
| P-109-DS | 128 ± 25 (IC) |
| P-110-DS | 35 ± 11 (IC) |
| P-123-DS | 49 ± 22 (IC) |
| P-136-DS | 106 ± 72 (IC) |
| P-141-DS | 120 ± 120 (PO) |
| P-169-DS | 19 ± 33 (IC) |
| P-9A-DS | 116 ± 48 (IC) |
| P-ØA-DS | 11 ± 2 (PO), 27 ± 27 (IC) |

EXAMPLES 4

Recombinant Human Growth Hormone Dosing Solutions

Intracolonic dosing compositions containing 25 mg/kg of carrier and 1 mg/kg of rHGH in phosphate buffer or oral gavage dosing solutions containing 600 mg/kg of carrier and 3 mg/kg of rHGH in phosphate buffer were prepared with carriers 9, 35, 36, 47, 62, 64, 67, 77, 79, 90, 94, 107, 109, 136, and 141.

The dosing solutions are designated R-carrier number-DS.

COMPARATIVE EXAMPLE 4A

Recombinant Human Growth Hormone Dosing Solutions

An intracolonic dosing solution was prepared according to the procedure of Example 4, substituting a carrier having the formula

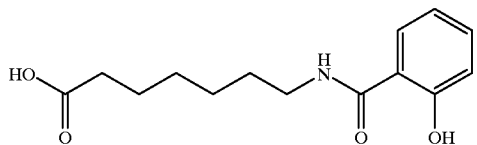

for the carrier. This dosing solution is designated as R-35A-DS.

COMPARATIVE EXAMPLE 4B

Recombinant Human Growth Hormone Dosing Solutions

An intracolonic dosing solution was prepared according to the procedure of Example 4, substituting a carrier having the formula

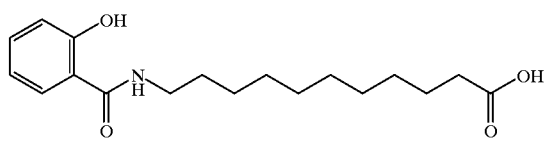

for the carrier. This dosing solution is designated as R-35B-DS.

COMPARATIVE EXAMPLE 4C

Recombinant Human Growth Hormone Dosing Solutions

An intracolonic dosing solution was prepared according to the procedure of Example 4, substituting a carrier having the formula

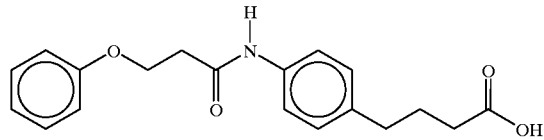

for the carrier. This dosing solution is designated as R-9A-DS.

EXAMPLE 5

In Vivo Recombinant Human Growth Hormone Delivery

Male Sprague-Dawley rats weighing 200–250 g were fasted for 24 hours and administered ketamine (44 mg/kg) and chlorpromazine (1.5 mg/kg) 15 minutes prior to dosing. The rats were administered one of the dosing solutions of Example 3 by either oral gavage or intracolonic instillation. Blood samples were collected serially from the tail artery for determination of serum rHGH concentrations. Serum rHGH concentrations were quantified by an rHGH immunoassay test kit.

Results are illustrated in Table 3, below.

COMPARATIVE EXAMPLE 5A

In Vivo Recombinant Human Growth Hormone Delivery

The procedure of Example 5 was followed, substituting the dosing solutions of Comparative Examples 3A–3C for the dosing solutions. Results are illustrated in Table 3, below.

COMPARATIVE EXAMPLE 5B

In Vivo Recombinant Human Growth Hormone Delivery

The procedure of Example 5 was followed, with dosing solutions of active agent (at a dose of 1 mg of rHGH/kg (intracolonic) or 3 mg of rHGH/kg (oral) and no carrier. These dosing solutions are designated R-ØD-DS and R-ØE-DS, respectively. Results are illustrated in Table 3, below.

TABLE 3

In Vivo Recombinant Human Growth Hormone Delivery

| Dosing Solution | Mean Peak Serum [rHGH] ± Standard Deviation (ng/ml) |
|---|---|
| R-9-DS | 125 ± 34 (IC) |
| R-35-DS | 41 ± 46 (PO) |
| | 108 ± 56 (IC) |
| R-36-DS | 28 ± 11 (IC) |
| R-47-DS | 0 (IC) |
| R-62-DS | 11 ± 12 (IC) |
| R-64-DS | 72 ± 22 (PO) |
| R-67-DS | 19 ± 22 (PO) |
| | 88 ± 24 (IC) |
| R-77-DS | 34 ± 10 (PO) |
| R-79-DS | 62 ± 51 (PO) |
| R-90-DS | 9 ± 13 (PO) |
| R-94-DS | 39 ± 35 (PO) |
| R-107-DS | 0 ± 0 (PO) |
| R-109-DS | 128 ± 25 (IC) |
| R-136-DS | 106 ± 72 (IC) |
| R-141-DS | 95 ± 14 (IC) |
| R-35A-DS | 17 ± 3 (IC) |
| R-35B-DS | 42 ± 28 (IC) |
| R-9A-DS | 55 ± 17 (IC) |

TABLE 3-continued

In Vivo Recombinant Human Growth Hormone Delivery

| Dosing Solution | Mean Peak Serum [rHGH] ± Standard Deviation (ng/ml) |
|---|---|
| R-⌀D-DS | 0 ± 0 (IC) |
| R-⌀E-DS | 0 ± 0 (IC) |

EXAMPLE 6
In Vivo Interferon Delivery

An intracolonic dosing composition containing 50 mg/kg of carrier 9 and 250 μg/kg of interferon in 50% propylene glycol was prepared. Rats were administered the dosing composition by intracolonic instillation. Delivery was evaluated by use of an ELISA assay for human interferon α from Biosource, Inc. Mean peak serum interferon concentration was 2611±695.

COMPARATIVE EXAMPLE 6A
In Vivo Interferon Delivery

Rats were administered, orally and by intracolonic instillation, dosing solutions of 1 mg/kg of interferon and no carrier. Delivery was evaluated according to the procedure of Example 6. Mean peak serum interferon concentration was 1951±1857 (PO) and 79±100 (IC).

EXAMPLE 7
Heparin Dosing Solutions

Intracolonic dosing compositions containing 50 mg/kg of carrier and 25 mg/kg of heparin in 25% aqueous propylene glycol or oral gavage dosing solutions containing 300 mg/kg of carrier and 100 mg/kg of heparin in 25% aqueous propylene glycol were prepared with carriers 9, 35, 47, 50, 58, 62, 64, 67, 76, 96, 102, 109, 110, 111, 117, 122, 123, 139, 141, 144, and 169. The dosing solutions are designated H-carrier number-DS.

COMPARATIVE EXAMPLE 7A
Heparin Dosing Solutions

Comparative intracolonic dosing compositions were prepared according to the procedure of Example 7, substituting the following carriers for the carrier.

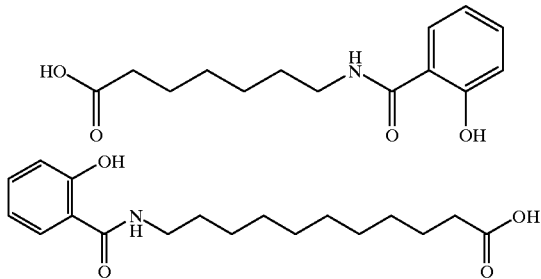

These dosing solutions are designated H-35A-DS, H-35B-DS, and H-109A-DS, respectively.

EXAMPLES 8
In Vivo Evaluation of Heparin in Rats

The dosing solutions of Example 7 were administered to fasted rats either by oral gavage or intracolonic instillation. Blood samples were collected by cardiac puncture following the administration of ketamine (44 mg/kg). Heparin activity was determined by utilizing the activated partial thromboplastin time (APTT) according to the method of Henry, J. B., Clinical Diagnosis and Management by Laboratory Methods; Philadelphia, Pa.; W. B. Saunders (1979).

Results are in illustrated in Table 4, below.

COMPARATIVE EXAMPLES 8A
In Vivo Evaluation of Heparin in Rats

The dosing solutions of Comparative Example 7A were administered to fasted rats by intracolonic instillation. Blood samples were collected and heparin activity was determined by the method of Example 8.

Results are illustrated in Table 4, below.

COMPARATIVE EXAMPLE 8B
In Vivo Evaluation of Heparin in Rats

An intracolonic dosing solution of 25 mg/kg of heparin and an oral gavage dosing solution of 100 mg/kg of heparin were administered to fasted rats. These dosage solutions were designated H-⌀A-DS and H-⌀B-DS, respectively.

Blood samples were collected, and heparin activity was determined by the methods of Example 8.

Results are illustrated in Table 4, below.

TABLE 4

| In Vivo Evaluation of Heparin in Rats | |
|---|---|
| Dosing Solution | Heparin APTT (sec) |
| H-9-DS | 48 ± 18 (IC) |
| H-35-DS | 54 ± 27 (PO), 177 ± 85 (IC) |
| H-47-DS | 30 ± 14 (IC) |
| H-50-DS | 40 ± 22 (IC) |
| H-58-DS | 24 ± 4 (IC) |
| H-62-DS | 37 ± 13 (IC) |
| H-64-DS | 59 ± 28 (PO), 168 ± 75 (IC) |
| H-67-DS | 76 ± 36 (IC) |
| H-76-DS | 63 ± 27 (PO) |
| H-96-DS | 36 ± 8 (IC) |
| H-102-DS | 111 ± 108 (IC) |
| H-109-DS | 56 ± 28 (IC) |
| H-110-DS | 37 ± 9 (IC) |
| H-111-DS | 71 ± 39 (IC) |
| H-117-DS | 140 ± 128 (IC) |
| H-122-DS | 49 ± 21 (IC), 207 ± 7 (PO) |
| H-123-DS | 42 ± 14 (PO) |
| H-139-DS | 31 ± 11 (IC) |
| H-141-DS | 59 ± 26 (IC) |
| H-144-DS | 26 ± 3 (IC) |
| H-35A-DS | 61 ± 29 (IC) |
| H-35B-DS | 51 ± 30 (IC) |
| H-169-DS | 23 ± 2 (IC) |
| H-⌀A-DS | 23 ± 2 (PO) |
| H-⌀B-DS | 33 ± 6 (IC) |

The above mentioned patents, applications, test methods, and publications are hereby incorporated by reference in their entirety.

Many variations of the present invention will suggest themselves to those skilled in the art in light of the above detailed description. All such obvious variations are within the full intended scope of the appended claims.

What is claimed is:

1. A composition comprising:
   (A) at least one active agent; and
   (B) a compound having the following formula

[Structure 141: 2-hydroxy-4-chloro-phenyl group connected via NH-C(=O)- to a heptamethylene chain ending in -C(=O)OH]

or a salt thereof.

2. A composition as defined in claim 1, wherein said active agent is selected from the group consisting of a biologically active agent, a chemically active agent, or a combination thereof.

3. A composition as defined in claim 2, wherein said biologically active agent comprises at least one peptide, mucopolysaccharide, carbohydrate, or lipid.

4. A composition as defined in claim 2, wherein said biologically active agent is selected from the group consisting of human growth hormone, bovine growth hormone, growth hormone-releasing hormone, an interferon, interleukin-II, insulin, heparin, low molecular weight heparin, calcitonin, erythropoietin, atrial naturetic factor, an antigen, a monoclonal antibody, samatostatin, adrenocorticotropin, gonadotropin releasing hormone, oxytocin, vasopressin, cromolyn sodium, vancomycin, parathyroid hormone, desferrioxamine (DFO), or any combination thereof.

5. A composition as defined in claim 4, wherein said biologically active agent comprises an interferon, interleukin-II, insulin, heparin, low molecular weight heparin, calcitonin, oxytosin, vasopressin, vancomycin, DFO, parathyroid hormone, and combinations thereof.

6. A composition as defined in claim 2, wherein said biologically active agent comprises parathyroid hormone.

7. A composition as defined in claim 2, wherein said biologically active agent comprises recombinant human growth hormone.

8. A composition as defined in claim 2, wherein said biologically active agent comprises heparin.

9. A composition as defined in claim 2, wherein said biologically active agent comprises low molecular weight heparin.

10. A method for administering a biologically-active agent to an animal in need of said agent, said method comprising administering orally to said animal a composition as defined in claim 2.

11. A dosage unit form comprising:
    (A) a composition as defined in claim 1; and
    (B)
       (a) an excipient
       (b) a diluent,
       (c) a disintegrant,
       (d) a lubricant,
       (e) a plasticizer,
       (f) a colorant,
       (g) a dosing vehicle, or
       (h) any combination thereof.

12. A composition as defined in claim 11, wherein said active agent is selected from the group consisting of a biologically active agent, a chemically active agent, or a combination thereof.

13. A composition as defined in claim 12, wherein said biologically active agent comprises at least one peptide, mucopolysaccharide, carbohydrate, or lipid.

14. A composition as defined in claim 12, wherein said biologically active agent is selected from the group consisting of human growth hormone, bovine growth hormone, growth hormone-releasing hormone, an interferon, interleukin-II, insulin, heparin, low molecular weight heparin, calcitonin, erythropoietin, atrial naturetic factor, an antigen, a monoclonal antibody, samatostatin, adrenocorticotropin, gonadotropin releasing hormone, oxytocin, vasopressin, cromolyn sodium, vancomycin, parathyroid hormone, desferrioxamine (DFO), or any combination thereof.

15. A composition as defined in claim 14, wherein said biologically active agent comprises an interferon, interleukin-II, insulin, heparin, low molecular weight heparin, calcitonin, oxytosin, vasopressin, vancomycin, DFO, parathyroid hormone, and combinations thereof.

16. A composition as defined in claim 11, wherein said biologically active agent comprises parathyroid hormone.

17. A composition as defined in claim 11, wherein said biologically active agent comprises recombinant human growth hormone.

18. A composition as defined in claim 11, wherein said biologically active agent comprises heparin.

19. A composition as defined in claim 11, wherein said biologically active agent comprises low molecular weight heparin.

20. A dosage unit form as defined in claim 11, comprising a tablet, a capsule, or a liquid.

21. A dosage unit form as defined in claim 20, wherein said dosing vehicle is selected from the group consisting of water, 1,2-propane diol, ethanol, or any combination thereof.

22. A compound having the formula

[Structure 141: 2-hydroxy-4-chloro-phenyl group connected via NH-C(=O)- to a heptamethylene chain ending in -C(=O)OH]

or a salt thereof.

23. A method for preparing a composition, said method comprising mixing:
    (A) at least one active agent;
    (B) at least one carrier compound as defined in claim 22; and
    (C) optionally, a dosing vehicle.

24. A composition comprising:
    (A) at least one active agent; and
    (B) a poly(amino acid) comprising a compound as defined in claim 22.

25. A composition as defined in claim 24, wherein said poly(amino acid) comprises a polypeptide.

* * * * *